US006770744B2

(12) United States Patent
Lollar

(10) Patent No.: US 6,770,744 B2

(45) Date of Patent: Aug. 3, 2004

(54) MODIFIED FACTOR VIII

(75) Inventor: John S. Lollar, Decatur, GA (US)

(73) Assignee: Emory University, Atlanta, GA (US)

(*) Notice: Subject to any disclaimer, the term of this patent is extended or adjusted under 35 U.S.C. 154(b) by 195 days.

(21) Appl. No.: 09/957,641

(22) Filed: Sep. 19, 2001

(65) Prior Publication Data

US 2002/0182670 A1 Dec. 5, 2002

Related U.S. Application Data

(60) Provisional application No. 60/236,460, filed on Sep. 29, 2000, and provisional application No. 60/234,047, filed on Sep. 19, 2000.

(51) Int. Cl.[7] ........................ A61K 35/14; A61K 35/16; C12N 15/00

(52) U.S. Cl. ..................... 530/383; 435/69.1; 435/69.6; 435/13; 435/7.1; 435/183; 514/2; 514/12; 514/802; 514/834; 530/380; 530/381; 930/10; 930/100

(58) Field of Search ............................... 435/69.1, 69.6, 435/13, 7.1, 183; 514/2, 12, 802, 834; 530/380, 381, 383; 930/10, 100

(56) References Cited

U.S. PATENT DOCUMENTS 5,663,060 A * 9/1997 Lollar et al. ............... 435/69.6
5,744,446 A 4/1998 Lollar et al.
5,859,204 A 1/1999 Lollar
6,180,371 B1 1/2001 Lollar ........................ 435/69.6
6,251,632 B1 * 6/2001 Lillicrap et al. ........... 435/69.1

OTHER PUBLICATIONS

Gilbert G. et al. (Nov. 2000) "Four hydrophobic amino acids of the factor VIII C2 domain contribute to the membrane binding motif" *Blood* 96(11):633a.

Healey J.F. et al. (1998) Residues Glu2181–Val2243 contain a major determinant of the inhibitory epitope in the C2 domain of human factor VIII *Blood* 92:3701–3709.

Jacquemin, M.G. et al. (1998) "Mechanism and kinetics of factor VIII inactivation: study with an IgG4 monoclonal antibody derived from a hemophilia A patient with inhibitor" *Blood* 92:496–506.

Kim, S.W. et al. (2000) "Identification of functionally important amino acid residues within the C2–domain of human factor V using alanine–scanning mutagenesis" *Biochemistry* 39:1951–1958.

Lin, S.W. et al. (Dec. 1993) "Characterization of Genomic Defects of hemophilia A in patients of Chinese origin" *Genomics* 18(3):496–504.

Lind, P. et al. (1995) "Novel forms of B–domain–deleted recombinant factor VIII molecules. Construction and biochemical characterization" *Eur. J. Biochem.* 232:19–27.

Macedo–Ribeiro, S. et al., (1999) "Crystal structures of the membrane–binding C2 domain of human coagulation factor V" *Nature* 402:434–439.

Ortel T.L. et al., (1998) "Inhibitory anti–factor V antibodies bind to the factor V C2 domain and are associated with hemorrhagic manifestations" *Blood* 91:4188–4196.

Ortel, T.L. et al. (1994) "Localization of functionally important epitopes within the second C–type domain of coagulation factor V using recombinant chimeras" *J. Biol. Chem.* 269:15898–15905.

Pratt K.P. (1999) "Structure of the C2 domain of human factor VIII at 1.5 Å resolution" *Nature* 402:439–442.

Prescott, R. et al. (1997) "The inhibitory antibody response is more complex in hemophilia A patients than in most nonhemophiliacs with fVIII autoantibodies" Blood 89:3663–3671.

Sawamoto, Y. et al. (1998) "C2 domain restricted epitope specificity of inhibitor antibodies elicited by a heat pasteurized product, factor VIII CSP–P, in previously treated hemophilia A patients without inhibitors" *Thromb. Haemostas.* 79:62–68.

Scandella et al. (1988) *Proc. Natl. Acad. Sci. USA* 85:6152–6156.

Shima, M.D. et al. (1993) "A factor VIII neutralizing monoclonal antibody and a human inhibitor alloantibody recognizing epitopes in the C2 domain inhibit factor VIII binding to von Willebrand factor and to phosphatidylserine" *Thromb. Haemost.* 69:240–246.

Arai, M. et al. (1989) "Molecular basis of factor–VIII inhibition by human antibodies—antibodies that bind to the factor–VIII light chain prevent the interaction of factor–VIII with phospholipid" *J. Clin. Invest.* 83:1978–1984.

Barrow, R. T. et al. (2000) "Reduction of the antigenicity of factor VIII toward complex inhibitory plasmas using multiply–substituted hybrid human/porcine factor VIII molecules" Blood 95:557–561.

Barrowcliffe, T. W. et al. (1983) "Binding to phospholipid protects factor VIII from inactivation by human antibodies" *J. Lab. Clin. Med.* 101:34–43.

Fulcher C.A. et al. (1985) "Localization of human factor FVIII inhibitor epitopes to two polypeptide fragments" *Proc. Natl. Acad. Sci. USA* 82:7728–7732.

Lubin, I.M. et al. (1994) "Elimination of a Major Inhibitor Epitope in Factor VIII"; *J. Biol. Chem.* 269:8639–8641.

* cited by examiner

*Primary Examiner*—Robert A. Wax
*Assistant Examiner*—Holly Schnizer
(74) *Attorney, Agent, or Firm*—Greenlee Winner and Sullivan PC

(57) ABSTRACT

Specific amino acid loci of human factor VIII interact with inhibitory antibodies of hemophilia patients after being treated with factor VIII. Modified factor VIII is disclosed in which the amino acid sequence is changed by a substitution at one or more of the specific loci. The modified factor VIII is useful for hemophiliacs, either to avoid or prevent the action of inhibitory antibodies.

43 Claims, 7 Drawing Sheets

| | 2173 | 2181 | 2191 |
|---|---|---|---|
| HF8 | SCSMPLGM | ESKAISDAQI | TASSYFTN**MF** |
| PF8 | SCSMPLGM | QNKAISDSQI | TASSHLSN**IF** |
| MF8 | SCSIPLGM | ESKVISDTQI | TASSYFTN**MF** |
| CF8 | SCSMPLGM | ESKAISDAQI | TASSYLSS**ML** |

| | 2201 | 2211 | 2221 |
|---|---|---|---|
| HF8 | ATWSPSKARL | HLQG**R**SNAW**R** | PQ**V**NNP**K**EWL |
| PFI | ATWSPSQARL | HLQG**R**TNAW**R** | PR**V**SSA**E**EWL |
| MF8 | ATWSPSQARL | HLQG**R**TNAW**R** | PQ**V**NDP**K**QWL |
| CF8 | ATWSPSQARL | HLQG**R**TNAW**R** | PQ**A**NNP**K**EWL |

| | 2231 | 2241 | 2251 |
|---|---|---|---|
| HF8 | QVDFQKTMKV | TGVTTQGV**K**S | **LL**TSMYVKEF |
| PF8 | QVDLQKTVKV | TGITTQGV**K**S | **LL**SSMYVKEF |
| MF8 | QVDLQKTMKV | TGIITQGV**K**S | **LF**TSMFVKEF |
| CF8 | QVDFRKTMKV | TGITTQGV**K**S | **LL**ISMYVKEF |

| | 2261 | 2271 | 2281 |
|---|---|---|---|
| HF8 | LISSSQDGHQ | WTLFFQNGKV | KVFQGNQDSF |
| PF8 | LVSSSQDGRR | WTLFLQDGHT | KVFQGNQDSS |
| MF8 | LISSSQDGHH | WTQILYNGKV | KVFQGNQDSS |
| CF8 | LISSSQDGHN | QTLFLQNGKV | KVFQGNRDSS |

| | 2291 | 2301 | 2311 |
|---|---|---|---|
| HF8 | TPVVNSLDPP | LLTRYLRIHP | QSWVHQIALR |
| PF8 | TPVVNALDPP | LFTRYLRIHP | TSWAQHIALR |
| MF8 | TPMMNSLDPP | LLTRYLRIHP | QIWEHQIALR |
| CF8 | TPVRNRLEPP | LVARYVRLHP | QSWAHHIALR |

| | 2321 | 2331 |
|---|---|---|
| HF8 | MEVLGCEAQD | LY |
| PF8 | LEVLGCEAQD | LY |
| MF8 | LEILGCEAQQ | QY |
| CF8 | LEVLGCDTQQ | PA |

FIG. 1

MODIFIED FACTOR VIII

CROSS-REFERENCE TO RELATED APPLICATIONS

This application claims priority under 35 U.S.C. § 119(e) to U.S. Provisional Applications 60/236,460 filed Sep. 29, 2000, and 60/234,047 filed Sep. 19, 2000, both of which are hereby incorporated by reference to the extent not inconsistent with the disclosure herein.

ACKNOWLEDGMENT OF FEDERAL RESEARCH SUPPORT

This invention was made, at least in part, with funding from the National Institutes of Health under contract No. FO1-HL46215. Accordingly, the U.S. government may have certain rights in this invention.

FIELD OF THE INVENTION

This invention relates generally to a modified mammalian factor VIII having amino acid substitutions which reduce its immunogenicity and/or antigenicity as compared to the proteins from which they were derived or other factor VIII preparations such as human factor VIII.

BACKGROUND OF THE INVENTION

Blood clotting begins when platelets adhere to the cut wall of an injured blood vessel at a lesion site. Subsequently, in a cascade of enzymatically regulated reactions, soluble fibrinogen molecules are converted by the enzyme thrombin to insoluble strands of fibrin that hold the platelets together in a thrombus. At each step in the cascade, a protein precursor is converted to a protease that cleaves the next protein precursor in the series. Co-factors are required at most of the steps.

Factor VIII circulates as an inactive precursor in blood, bound tightly and non-covalently to von Willebrand factor. Factor VIII is proteolytically activated by thrombin or factor Xa, which dissociates it from von Willebrand factor and activates its procoagulant function in the cascade. In its active form, the protein factor VIIIa is a cofactor that increases the catalytic efficiency of factor IXa toward factor X activation by several orders of magnitude.

People with deficiencies in factor VIII or antibodies against factor VIII who are not treated with factor VIII suffer uncontrolled internal bleeding that may cause a range of serious symptoms, from inflammatory reactions in joints to early death. Severe hemophiliacs, who number about 10,000 in the United States, can be treated with infusion of human factor VIII, which will restore the blood's normal clotting ability if administered with sufficient frequency and concentration. The classical definition of factor VIII is that substance present in normal blood plasma that corrects the clotting defect in plasma derived from individuals with hemophilia A.

The development of antibodies ("inhibitors" or "inhibitory antibodies") that inhibit the activity of factor VIII is a serious complication in the management of patients with hemophilia. Autoantibodies develop in approximately 20% of patients with hemophilia A in response to therapeutic infusions of factor VIII. In previously untreated patients with hemophilia A who develop inhibitors, the inhibitors usually develops within one year of treatment. Additionally, autoantibodies that inactivate factor VIII occasionally develop in individuals with previously normal factor VIII levels. Inhibitory antibodies (inhibitors) to factor VIII (fVIII) either develop as alloantibodies in hemophilia A patients following fVIII infusions or as autoantibodies in nonhemophiliacs (Hoyer, L. W. and D. Scandella, 1994, "Factor VIII inhibitors: structure and function in autoantibody and hemophilia A patients," *Semin.Hematol.* 31:1–5). Antibodies to epitopes in the A2, ap-A3, and C2 domains within the A1-A2-B-ap-A3-C1-C2 fVIII molecule are responsible for all anticoagulant activity in most inhibitor plasmas (Prescott, R. et al., 1997, "The inhibitory antibody response is more complex in hemophilia A patients than in most nonhemophiliacs with fVIII autoantibodies," *Blood* 89:3663–3671; Barrow, R. T. et al., 2000, "Reduction of the antigenicity of factor VIII toward complex inhibitory plasmas using multiply-substituted hybrid human/porcine factor VIII molecules," *Blood* 95:557–561). The 18-kDa C2 domain, defined as residues Ser2173-Tyr2332 in single chain human fVIII, contains a phospholipid membrane-binding site that is necessary for the normal procoagulant function of fVIII. Human C2-specific anti-fVIII antibodies inhibit this interaction (Arai, M. et al., 1989, "Molecular basis offactor-VIII inhibition by human antibodies—antibodies that bind to the factor-VIII light chain prevent the interaction of factor-VIII with phospholipid," *J. Clin. Invest.* 83:1978–1984). Consistent with this, phospholipid protects fVIII from inactivation by fVIII inhibitors (Arai et al., supra; Barrowcliffe, T. W. et al., 1983, "Binding to phospholipid protects factor VIII from inactivation by human antibodies," *J. Lab. Clin. Med.* 101:34–43). The C2 domain also contains part of the von Willebrand factor (vWf) binding site (Saenko, E. L. et al., 1994, "A role for the C2 domain of factor binding to von Willebrand factor. *J. Biol. Chem.* 269:11601–11605; Saenko, E. L. and Scandella, D., 1997, "The acidic region of the factor VIII light chain and the C2 domain together form the high affinity binding site for von Willebrand factor," *J. Biol. Chem.* 272:18007–18014). Some inhibitors may act by interfering with this interaction (Shima, M. et al., 1995, "Common inhibitory effects of human anti-C2 domain inhibitor alloantibodies on factor VIII binding to von Willebrand factor," *Br. J. Haematol.* 91:714–721; Saenko, E. L. et al., 1996, "Slowed release of thrombin-cleaved factor VIII from von Willebrand factor by a monoclonal and human antibody is a novel mechanism for factor VIII inhibition," *J. Biol. Chem.* 271:27424–27431; Gilles, J G. et al., 1999, "Some factor VIII (FVIII) inhibitors recognize a FVIII epitope(s) that is present only on FVIII-vWf complexes," *Thromb. Haemost.* 82:40–45).

Patients can be managed by increasing the dose of factor VIII provided the inhibitor titer is low enough. However, often the inhibitor titer is so high that it cannot be overwhelmed by factor VIII. An alternative strategy is to bypass the need for factor VIII during normal hemostasis using factor IX complex preparations (for example, KONYNE®, Proplex®) or recombinant human factor VIIIa. Additionally, since porcine factor VIII usually has substantially less reactivity with inhibitors than human factor VIII, a partially purified porcine factor VIII preparation (HYATE:C®) is used. Many patients who have developed inhibitory antibodies to human factor VIII have been successfully treated with porcine factor VIII and have tolerated such treatment for long periods of time. However, administration of porcine factor VIII is not a complete solution because inhibitors may develop to porcine factor VIII after one or more infusions.

Several preparations of human plasma-derived factor VIII of varying degrees of purity are available commercially for the treatment of hemophilia A. These include a partially-purified factor VIII derived from the pooled blood of many donors that is heat- and detergent-treated for viruses but contain a significant level of antigenic proteins; a monoclonal antibody-purified factor VIII that has lower levels of antigenic impurities and viral contamination; and recombinant human factor VIII, clinical trials for which are underway. Unfortunately, human factor VIII is unstable at physiologic concentrations and pH, is present in blood at an extremely low concentration (0.2 μg/ml plasma), and has low specific clotting activity.

Hemophiliacs require daily replacement offactor VIII to prevent bleeding and the resulting deforming hemophilic arthropathy. However, supplies have been inadequate and problems in therapeutic use occur due to difficulty in isolation and purification, immunogenicity, and the necessity of removing the AIDS and hepatitis infectivity risk. The use of recombinant human factor VIII or partially-purified porcine factor VIII will not resolve all the problems.

The problems associated with the commonly used, commercially available, plasma-derived factor VIII have stimulated significant interest in the development of a better factor VIII product. There is a need for a more potent factor VIII molecule so that more units of clotting activity can be delivered per molecule; a factor VIII molecule that is stable at a selected pH and physiologic concentration; a factor VIII molecule that is less apt to cause production of inhibitory antibodies; and a factor VIII molecule that evades immune detection in patients who have already acquired antibodies to human factor VIII.

U.S. Pat. No. 6,180,371 to Lollar describes amino acid substitutions in the A2 domain of human factor VIII which alter the antigenicity of the resulting factor VIII molecules. The '371 patent does not disclose or suggest specific amino acid substitutions in the C2 domain which reduces antigenicity or immunogenicity as compared to wild-type factor VIII or the corresponding recombinant factor VIII.

U.S. Pat. No. 5,859,204 to Lollar discloses the site specific replacement of amino acids in the 484–509 region of human factor VIII. More specifically, the '204 patent teaches modified factor VIII with amino acid substitutions at positions 485, 487, 488, 489, 492, 495, 501 or 508 relative to the human protein. The '204 patent does not disclose or suggest specific amino acid substitutions in the C2 domain which reduce antigenicity or immunogenicity as compared to wild-type factor VIII or the corresponding recombinant factor VIII.

U.S. Pat. No. 5,888,974 to Lollar et al. discloses hybrid procoagulant factor VIII produced by the isolation and recombination of human and other non-human factor VIII subunits or domains.

U.S. Pat. No. 5,744,446 to Lollar et al. describes hybrid factor VIII having amino acid substitutions in the A2 domain.

U.S. Pat. No. 5,663,060 to Lollar et al. describes hybrid factor VIII comprised of combinations of non-human and human heavy and light chain subunits. U.S. Pat. No. 5,583,209 describes nucleic acids encoding the hybrid factor VIII molecules in the '060 patent.

U.S. Pat. No. 5,364,771 describes purified hybrid factor VIII comprised of human and porcine combinations of the heavy and light subunits. Also disclosed is human factor VIII with porcine A2 domain swapped for the human A2 domain.

U.S. Pat. Nos. 6,180,371; 5,888,974; 5,859,204; 5,744,446; 5,663,060; 5,583,209; and 5,364,771 (all of which are incorporated herein by reference) do not disclose substitutions or suggest specific amino acid substitutions in the C2 domain of factor VIII which reduce antigenicity or immunogenicity as compared to wild-type factor VIII or the corresponding recombinant factor VIII. Despite years of intensive research from laboratories around the world, it appears that the invention regarding the C2 domain of factor VIII described in detail herein has not been described or suggested elsewhere.

Pratt et al. (1999, "Structure of the C2 domain of human factor VIII at 1.5 Å resolution," *Nature* 402:439–442) have reported the crystal structure of the C2 domain of human factor VIII at 1.5 Å resolution. Pratt et al. reported that the structure partly explains why mutations in the C2 region of factor VIII lead to bleeding disorders. In fact, 21 residues in the C2 region were reported to be sites of deleterious point mutations in patients with hemophilia A. For example, V2223 is known to be a position where a point mutation occurs and is associated with bleeding disorders. Thus, one of ordinary skill in the art would not expect V2223 to be a reasonable candidate for substitution to provide modified factor VIII for therapeutic activity. Indeed, Shima et al. report C2 binding antibody inhibitors interfere with factor VIII with respect to phospholipid and Von Willebrand factor binding. Thus, it is taught by Pratt et al. that C2 inhibitors, i.e., those related to some bleeding disorders in individuals with hemophilia A, interfere with the binding of the C2 domain to phospholipid and Von Willebrand factor. This conclusion, combined with their determination that M2199, F2200, L2251, L2252, V2223, and R2220 appear at the protein-phospholipid interface, suggests that mutation of these residues would lead to altered phospholipid and/or Von Willebrand binding along with an associated increase in bleeding disorders. It is not clear from these studies which amino acid residues and corresponding substitutions would lead to improved factor VIII molecules.

Unexpectedly it was discovered by the inventor of the instant invention that mutations in the 3 hydrophobic feet identified in the recently available x-ray structure for the C2 domain of factor VIII have reduced binding to inhibitory antibodies, improved properties, and/or reduced immunogenicity.

It is therefore an object of the present invention to provide a factor VIII that corrects hemophilia in a patient deficient in factor VIII or having inhibitors to factor VIII.

It is a further object of the present invention to provide methods for treatment of hemophiliacs.

It is still another object of the present invention to provide a factor VIII that is stable at a selected pH and physiologic concentration.

It is yet another object of the present invention to provide a factor VIII that has greater coagulant activity than human factor VIII.

SUMMARY OF THE INVENTION

The present invention generally relates to compositions comprising recombinant mammalian factor VIII. The composition of the invention comprise isolated, purified recombinant mammalian factor VIII molecules with coagulant activity wherein the recombinant factor VIII has amino acid substitutions in the C2 domain which reduce antigenicity as compared to the proteins from which they were derived or other factor VIII preparations. DNA sequences encoding the novel compositions of the invention as well as methods of producing the novel compositions comprising factor VIII are also provided. Methods of treating patients in need of treatment with factor VIII are also within the scope of this invention.

A first embodiment of the invention provides novel compositions comprising recombinant mammalian factor VIII with amino acid substitution(s) in the C2 domain. The amino acid substitution(s) in the C2 domain of the modified recombinant factor VIII reduce the anticoagulant activity of inhibitory antibodies as compared to the proteins from which they were derived or other available factor VIII preparations. The novel composition of this embodiment have coagulant activity and reduced binding to inhibitory antibodies. Substitutions at residues that participate in binding of fVIII to phospholipid membranes and/or to inhibitory antibodies are preferred. Preferred substitutions at positions homologous to human factor VIII include, but are not limited to, Met2199, Phe2200, Val2223, Leu2251, and Leu2252. The novel compositions of this embodiment can be a single mutant, a double mutant, a triple mutant, or a quadruple mutant. Examples of amino acid substitutions of the invention include, but are not limited to, Met2199Ile, Phe2200Leu, Leu2252Phe, Met2199Ile/Phe2200Leu, Val2223Ala/Lys2227Glu, Met2199Ile/Phe2200Leu/Va2223 Ala/Lys2227Glu, all of which are referenced to the human factor VIII numbering system wherein amino acid number 1 is the amino terminal alanine of mature factor VIII. Substitutions in either recombinant porcine or human factor VIII are preferred.

A second embodiment of the invention provides novel hybrid factor VIII compositions comprising recombinant factor VIII with amino acid substitution(s) in the C2 domain. The novel compositions of this embodiment are constructed by preparing hybrid factor VIII with amino acid substitutions in the C2 domain. The other domains of factor VIII may be derived from a variety of mammals such as human, mouse, pig, rat, and canine and so on. The novel compositions of this embodiment have coagulant activity and reduced binding to inhibitory antibodies. Examples of amino acid positions that can be mutated to provided the novel compositions of this embodiment include, but are not limited to, Met2199, Phe2200, Val2223, Leu2251, and Leu2252, all of which are referenced to human factor VIII. Examples of amino acid substitutions in the C2 domain encompassed within this embodiment include, but are not limited to, Met2199Ile, Phe2220Leu, Leu2252Phe, Met2199Ile/Phe2200Leu, Val2223Ala/Lys2227Glu, Met2199Ile/Phe2200Leu/-Val2223Ala/Lys2227Glu, all of which are referenced to the human factor VIII.

Another embodiment of the invention provides DNA sequences comprising coding sequences for the novel compositions of the invention. Yet another embodiment of the invention provides methods of producing the novel compositions of the invention.

The invention also provides a method for reducing the immunogenicity of factor VIII molecules as well as recombinant factor VIII with reduced immunogenicity produced by the method. In particular, modified recombinant factor VIII molecule and methods of making such molecules with reduced immunogenicity that have substitutions in the C2 domain are described.

Also provided are pharmaceutical compositions and methods for treating patients having factor VIII deficiency comprising administering recombinant factor VIII and hybrid version thereof.

BRIEF DESCRIPTION OF THE DRAWINGS

FIG. 1. Putative fVIII residues involved in phospholipid binding. Shown are aligned sequences of the C2 domains of human, HF8 (amino acid residues 2173 to 2332 in SEQ ID NO: 2),(Vehar, G. A. et al., supra, 1984; Toole, J. J. Ct al., 1984, "Molecular cloning of a cDNA encoding human antihaemophilic factor" *Nature* 312:342–347), porcine, PF8 (SEQ ID NO:19), (Healey, J. F. et al., 1996, "The cDNA and derived amino acid sequence of porcine factor VIII," *Blood* 88:4209–4214), murine, MF8 (SEQ ID NO: 20), (Elder, B. et al., 1993, "Sequence of the murine factor VIII cDNA," *Genomics* 16:374–379) and canine, CF8 (SEQ ID NO: 21), (Cameron, C. et al., 1998, "The canine factor VIII cDNA and 5' flanking sequence," *Thromb.Haemostas.* 79:317–322) fVIII. Proposed phospholipid-binding residues in human fVIII (Pratt, K. P. et al., 1999, "Structure of the C2 domain of human factor VIII at 1.5 Åresolution," *Nature* 402:439–442) and homologous residues are underlined and shown in bold.

DETAILED DESCRIPTION OF THE INVENTION

Figure 2A:
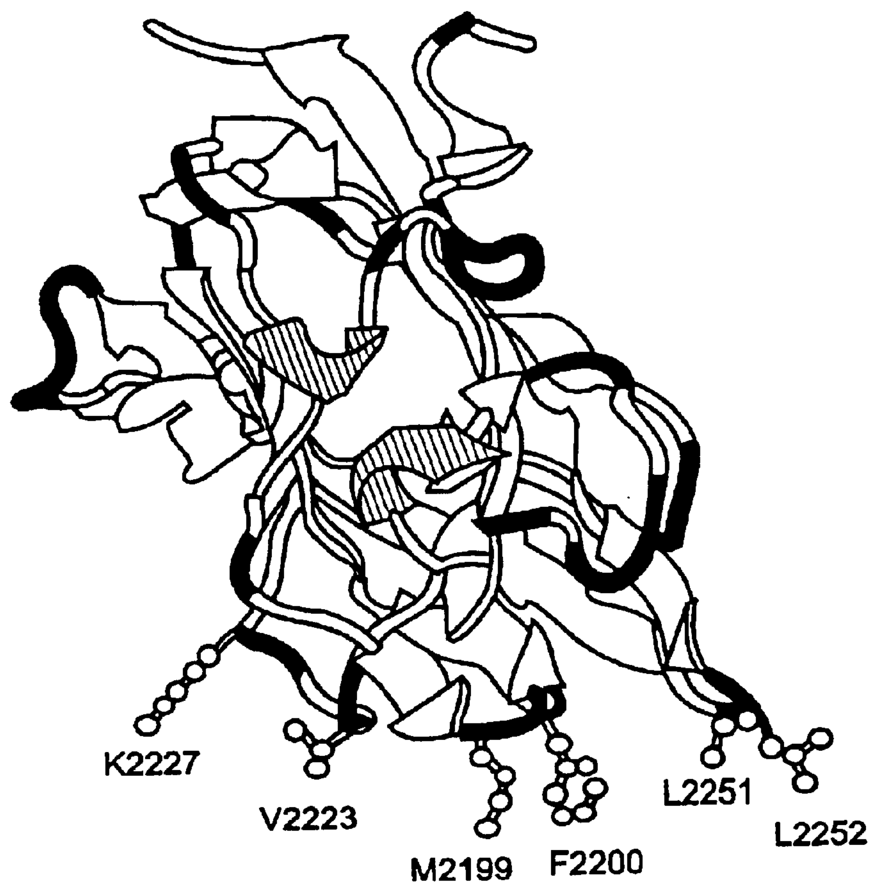
FIG. 2. Mutated sites in the human fVIII C2 domain. A. Ribbon diagram showing hydrophobic residues proposed to be involved in phospholipid membrane binding and Lys2227, one of the four putative positively-charged binding residues (Pratt, K. P. et al., 1999, "Structure of the C2 domain of human factor VIII at 1.5 Å resolution," *Nature* 402:439–442). Met2199, Phe2200, Val2223, Lys2227, and Leu2252 were mutated in this study. Leu2251, which is conserved in human, porcine, murine, and canine fVIII, was not mutated. B. Space filling model rotated, as if looking up from the membrane.

The present invention generally relates to compositions comprising recombinant mammalian factor VIII. The composition of the invention comprise isolated, purified recombinant mammalian factor VIII molecules with coagulant activity. It was surprisingly discovered that mutations in the C2 domain of factor VIII, in three hydrophobic feet identified in a recently available x-ray structure, reduced the binding of inhibitory antibodies of the mutants as compared to the proteins from which they were derived and/or other factor VIII preparations. Thus, the novel compositions of the invention comprise recombinant factor VIII with amino acid substitutions in the C2 domain which reduce antigenicity as compared to the proteins from which they were derived. Furthermore, the invention also provides recombinant factor VIII with amino acid substitutions in the C2 domain which reduce antigenicity as compared to other available factor VIII preparations. Related embodiments of the invention provide for methods of treating patients in need offactor VIII treatment, methods of producing the novel recombinant factor VIII compositions of the invention, DNA sequences comprising coding sequences of the novel recombinant factor VIII proteins, and pharmaceutical compositions comprising the novel factor VIII proteins.

The present invention further provides active recombinant hybrid factor VIII molecules or fragments thereof, the nucleic acid sequences encoding these hybrids, methods of preparing and isolating them, and methods for characterizing them. These hybrids comprise human/animal, animal/animal, or other such hybrid factor VIII molecules, and further comprise at least one specific amino acid sequence in the C2 domain including one or more unique amino acids of the factor VIII of one species substituted for the corresponding amino acid sequence (or amino acid) of the factor VIII of the other species; or comprises at least one sequence in the C2 domain including one or more amino acids having no known sequence identity to factor VIII substituted for specific amino acid sequence in human, animal, or hybrid factor VIII. The resulting recombinant hybrid factor VIII has reduced or no immunoreactivity to factor VIII inhibitory antibodies, compared to human or porcine factor VIII.

A "corresponding" nucleic acid or amino acid or sequence of either, as used herein, is one present at a site in a factor VIII molecule or fragment thereof that has the same structure and/or function as a site in the factor VIII molecule of another species, although the nucleic acid or amino acid number may not be identical. A DNA sequence "corresponding to" another factor VIII sequence substantially corresponds to such sequence, and hybridizes to the sequence of the designated SEQ ID NO. under stringent conditions. A DNA sequence "corresponding to" another factor VIII sequence also includes a sequence that results in the expression of a factor VIII or fragment thereof and would hybridize to the designated SEQ ID NO. but for the redundancy of the genetic code.

A "unique" amino acid residue or sequence, as used herein, refers to an amino acid sequence or residue in the factor VIII molecule of one species that is different from the homologous residue or sequence in the factor VIII molecule of another species.

"Specific activity," as used herein, refers to the activity that will correct the coagulation defect of human factor VIII deficient plasma. Specific activity is measured in units of clotting activity per milligram total factor VIII protein in a standard assay in which the clotting time of human factor VIII deficient plasma is compared to that of normal human plasma. One unit of factor VIII activity is the activity present in one milliliter of normal human plasma. In the assay, the shorter the time for clot formation, the greater the activity of the factor VIII being assayed. Porcine factor VIII has coagulation activity in a human factor VIII assay.

"Expression" refers to the set of processes that occur whereby genetic information is utilized to yield a product. A DNA encoding the amino acid sequence of porcine factor VIII can be "expressed" within a mammalian host cell to yield modified factor VIII protein. The materials, genetic structures, host cells and conditions which permit expression of a given DNA sequence to occur are well-known in the art and can be manipulated to affect the time and amount of expression, as well as the intra- or extra-cellular location of the expressed protein. For example, by including DNA encoding a signal peptide at the 5' end of the DNA encoding porcine factor VIII (the 5' end being, by convention, that end encoding the $NH_2$ terminus of the protein) the expressed protein becomes exported from the interior of the host cell into the culture medium. Providing a signal peptide coding DNA in combination with the porcine factor VIII coding DNA is advantageous because the expressed factor VIII is exported into the culture medium which simplifies the process of purification. A preferred signal peptide is a mammalian factor VIII signal peptide.

The human factor VIII cDNA nucleotide and predicted amino acid sequences are shown in SEQ ID NOs: 1 and 2, respectively. Factor VIII is synthesized as an approximately 300 kDa single chain protein with internal sequence homology that defines the "domain" sequence $NH_2$-A1-A2-B-A3-C1-C2-COOH. In a factor VIII molecule, a "domain", as used herein, is a continuous sequence of amino acids that is defined by internal amino acid sequence identity and sites of proteolytic cleavage by thrombin. Unless otherwise specified, factor VIII domains include the following amino acid residues, when the sequences are aligned with the human amino acid sequence (SEQ ID NO: 2): A1, residues Ala1-Arg372; A2, residues Ser373-Arg740; B, residues Ser741-Arg1648; A3, residues Ser1690-Ile2032; C1, residues Arg2033-Asn2172; C2, residues Ser2173-Tyr2332. The A3-C1-C2 sequence includes residues Ser1690-Tyr2332. The remaining segment, residues Glu1649-Arg1689, is usually referred to as the factor VIII light chain activation peptide. Factor VIII is proteolytically activated by thrombin or factor Xa, which dissociates it from von Willebrand factor, forming factor VIIIa, which has procoagulant function. The biological function of factor VIIIa is to increase the catalytic efficiency of factor IXa toward factor X activation by several orders of magnitude. Thrombin-activated factor VIIIa is a 160 kDa A1/A2/A3-C1-C2 heterotrimer that forms a complex with factor IXa and factor X on the surface of platelets or monocytes. A "partial domain" as used herein is a continuous sequence of amino acids forming part of a domain.

"Subunits" of human or animal factor VIII, as used herein, are the heavy and light chains of the protein. The heavy chain of factor VIII contains three domains, A1, A2, and B. The light chain of factor VIII also contains three domains, A3, C1, and C2.

The terms "epitope," "antigenic site," and "antigenic determinant," as used herein, are used synonymously and are defined as a portion of the human, or animal factor VIII or fragment thereof that is specifically recognized by an antibody. It can consist of any number of amino acid residues, and it can be dependent upon the primary, secondary, or tertiary structure of the protein.

The term "immunogenic site," as used herein, is defined as a region of the human or animal factor VIII, or fragment thereof, that specifically elicits the production of antibody to the factor VIII, or fragment, in a human or animal, as measured by routine protocols, such as immunoassay, e.g. ELISA, or the Bethesda assay, described herein. It can consist of any number of amino acid residues, and it can be dependent upon the primary, secondary, or tertiary structure of the protein. In some embodiments, the hybrid or hybrid equivalent factor VIII or fragment thereof is nonimmunogenic or less immunogenic in an animal or human than human or porcine factor VIII.

"Factor VIII deficiency," as used herein, includes deficiency in clotting activity caused by production of defective factor VIII, by inadequate or no production of factor VIII, or by partial or total inhibition of factor VIII by inhibitors. Hemophilia A is a type of factor VIII deficiency resulting from a defect in an X-linked gene and the absence or deficiency of the factor VIII protein it encodes.

As used herein, "diagnostic assays" include assays that in some manner utilize the antigen-antibody interaction to detect and/or quantify the amount of a particular antibody that is present in a test sample to assist in the selection of medical therapies. There are many such assays known to those of skill in the art. As used herein, human, porcine or modified porcine factor VIII DNA or fragment thereof and protein expressed therefrom, in whole or in part, can be substituted for the corresponding reagents in the otherwise known assays, whereby the modified assays may be used to detect and/or quantify antibodies to factor VIII. It is the use of these reagents, the factor VIII DNA or fragment thereof or protein expressed therefrom, that permits modification of known assays for detection of antibodies to human or animal factor VIII. Such assays include, but are not limited to ELISAs, immunodiffusion assays, and immunoblots. Suitable methods for practicing any of these assays are known to those of skill in the art. As used herein, the factor VIII or fragment thereof that includes at least one epitope of the protein can be used as the diagnostic reagent. Examples of other assays in which human, porcine or modified porcine factor VIII or fragment thereof can be used include the Bethesda assay and anticoagulation assays.

The term "DNA encoding a protein, such as porcine factor VIII" means a polydeoxynucleic acid whose nucleotide sequence embodies coding information to a host cell for the amino acid sequence of the protein, e.g. porcine factor VIII, according to the known relationships of the genetic code.

The "expression product" of a DNA encoding a human or animal factor VIII or a modified factor VIII is the product obtained from expression of the referenced DNA in a suitable host cell, including such features of pre- or post-translational modification of protein encoded by the referenced DNA, including but not limited to glycosylation, proteolytic cleavage and the like. It is known in the art that such modifications can occur and can differ somewhat depending upon host cell type and other factors, and can result in molecular isoforms of the product, with retention of procoagulant activity. See, e.g. Lind, P. et al., *Eur. J. Biochem.* 232:1927 (1995), incorporated herein by reference.

An "expression vector" is a DNA element, often of circular structure, having the ability to replicate autonomously in a desired host cell, or to integrate into a host cell genome and also possessing certain well-known features which permit expression of a coding DNA inserted into the vector sequence at the proper site and in proper orientation. Such features can include, but are not limited to, one or more promoter sequences to direct transcription initiation of the coding DNA and other DNA elements such as enhancers, polyadenylation sites and the like, all as well known in the art. The term "expression vector" is used to denote both a vector having a DNA coding sequence to be expressed inserted within its sequence, and a vector having the requisite expression control elements so arranged with respect to an insertion site that it can serve to express any coding DNA inserted into the site, all as well-known in the art. Thus, for example, a vector lacking a promoter can become an expression vector by the insertion of a promoter combined with a coding DNA.

Discovery of Mutations in Factor VIII Which Reduce Binding of Inhibitory Antibodies Recently, a 1.5 Å X-ray structure of the human fVIII C2 domain was reported (Pratt, K. P. et al., 1999, "Structure of the C2 domain of human factor VIII at 1.5 A resolution," *Nature* 402:439–442). Examination of this structure revealed three solvent-exposed hydrophobic "feet" consisting of Met2199/Phe2200, Val2223, and Leu2251/Leu2252. A ring of positively charged residues, including Arg 2213, Arg 2220, Lys 2227, and Lys 2249, surrounds these residues. This motif suggests that membrane binding consists of the insertion of the hydrophobic feet into the membrane bilayer and is stabilized by electrostatic interaction with negatively charged phospholipid.

Most fVIII inhibitors cross-react poorly with porcine fVIII. This observation led to the mapping of a major determinant of the C2 epitope to residues Glu2181-Val2243 using a series of constructs that contained porcine substitutions in the human fVIII C2 domain (Healey, J. F. et al., 1998, "Residues Glu2181-Val2243 contain a major determinant of the inhibitory epitope in the C2 domain of human factor VIII," *Blood* 92:3701–3709). In the present invention, residues in porcine, murine, or canine fVIII that are homologous to residues Met2199, Phe2200, Val2223, Lys2227, and/or Leu2252 in human fVIII were used as the basis for creating a series of recombinant fVIII molecules. A significant reduction in antigenicity was observed associated with mutations at Met2199, Phe2200, and Leu2252, indicating that these residues participate in binding of fVIII to phospholipid membranes and often to inhibitory antibodies.

Figure 2B:
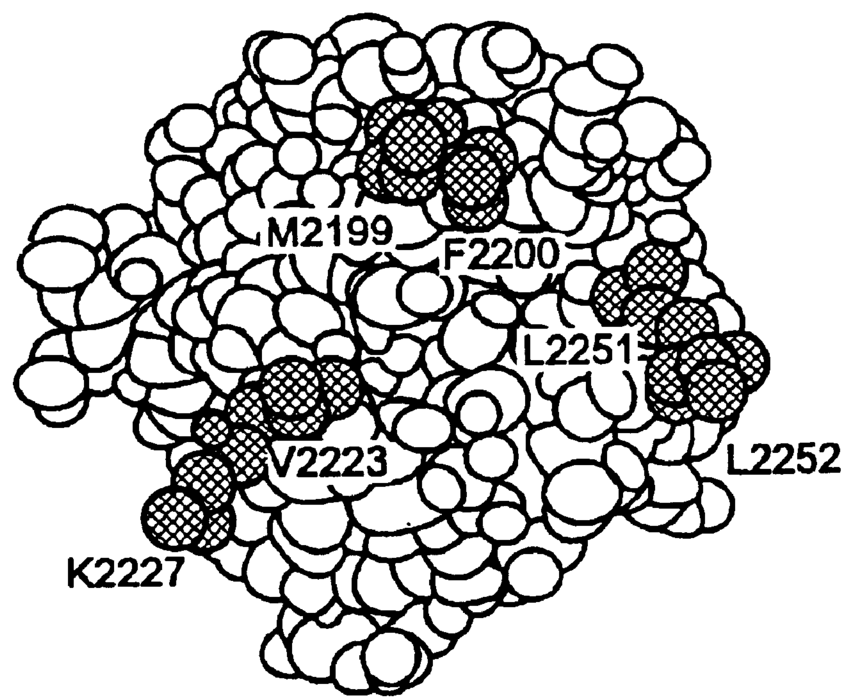
Figure 3A:
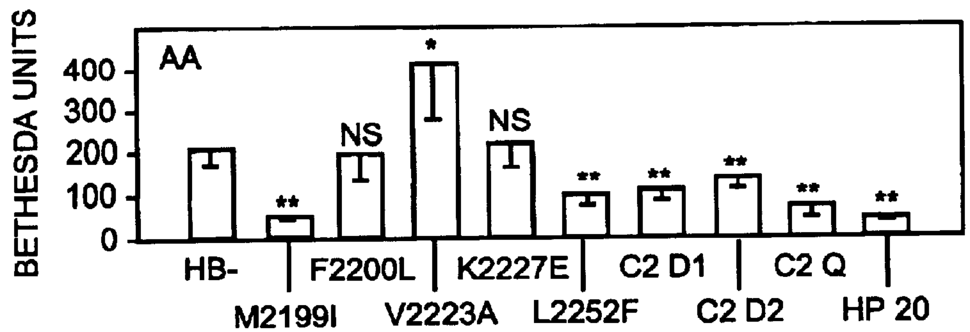
FIG. 3. Bethesda titers of patient polyclonal anti-fVIII antibodies. Recombinant fVIII was diluted into hemophilia A plasma and Bethesda titers of antibodies AA, AJ, HR, LK, and RvR were determined as described in "Materials and Methods". Shown are means and standard deviations determined by nonlinear least-squares regression analysis. C2 D1 is the Met2199Ile/Phe2200Leu double mutant. C2 D2 is the Val2223Ala/Lys2227Glu double mutant. C2 Q is the Met2199Ile/Phe2200Leu/Val2223Ala/Lys2227Glu quadruple mutant. HP20 is a B-domainless hybrid human/porcine fVIII molecule containing human A1, A2, ap-A3, and C1 domains and the porcine C2 domain. Confidence levels for differences between mutants and HB- are indicated as "**" at the 99.9% level and "*" at the 99% level. NS, not significant.
Figure 3B:
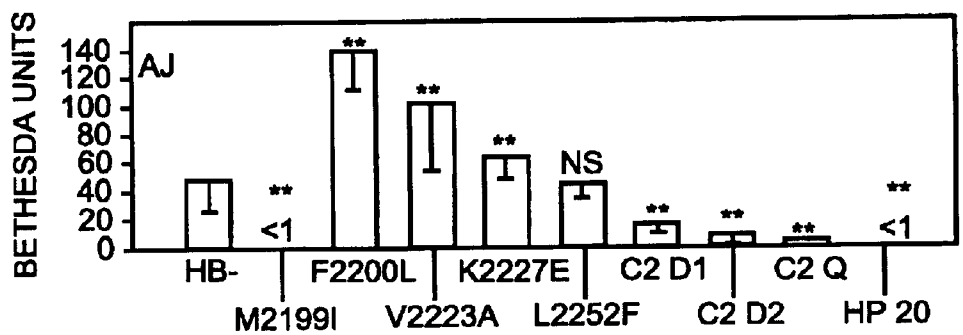
Figure 3C:
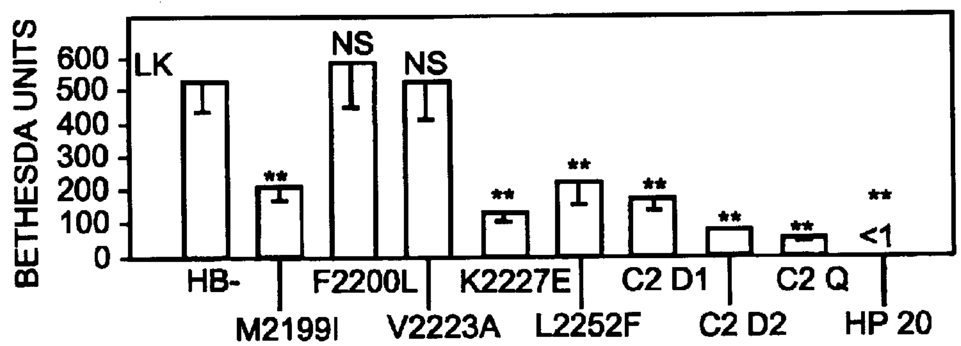
Figure 3D:
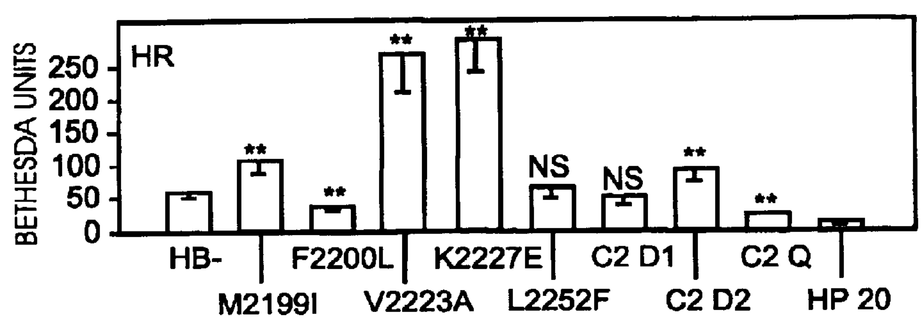
Figure 3E:
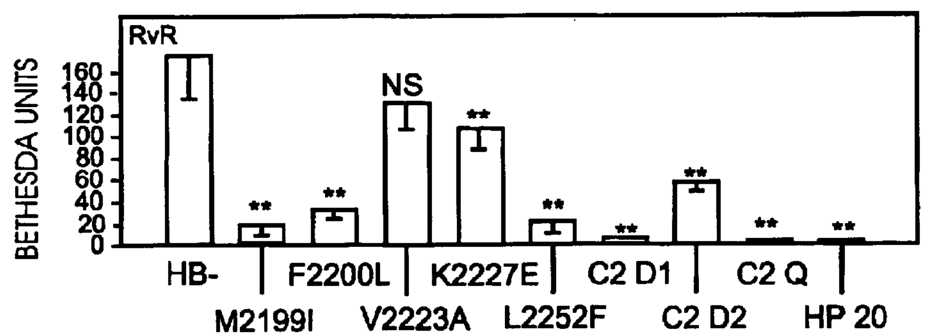

FIG. 1 shows the alignment of the human, porcine, murine and canine fVIII C2 domains. At four of the five proposed hydrophobic phospholipid binding residues there is one species that differs from human fVIII: Met2199→Ile (porcine), Phe2200→Leu (canine), Val2223→Ala (canine), and Leu2252→Phe (murine). There is a species difference in only one of the four proposed basic residues, Lys2227→Glu (porcine). Accordingly, Met2199Ile, Phe2200Leu, Val2223Ala, Leu2252Phe, and Lys2227Glu single mutants in human B-domainless fVIII were made. Additionally, two double mutants, Met2199Ile/Phe2200Leu (designated C2 D1) and is Val2223Ala/Leu2252Phe (C2 D2), and a quadruple mutant, Met2199Ile/Phe2200Leu/Val2223Ala/Leu2252Phe (C2 Q) were made. The locations of the mutated residues in the X-ray structure of fVIII are shown in FIG. 2. Met2199/Phe2200 and Leu2251/Leu2252 project from two β-hairpin loops. Val2223 projects from an adjacent loop and is near Lys2227.

The mutants were stably expressed in serum-free medium from a baby hamster kidney-derived cell line and then were partially purified. The specific coagulant activities of the hybrids based on an ELISA assay were equal or greater than that of HB- as described in "Materials and Methods", indicating that they were suitable for antigenicity studies. The interaction of the mutants with C2-specific fVIII inhibitors was measured using the Bethesda assay as described in "Materials and Methods". The results were compared to human B-domainless fVIII (HB-) and a hybrid human/porcine FVIII molecule, HP20, which is human except for substitution of the entire porcine C2 domain (Healey, J. F. et al., 1998, "Residues Glu2181-Val2243 contain a major determinant of the inhibitory epitope in the C2 domain of human factor VIII," *Blood* 92:3701–3709).

Most FVIII inhibitors are polyclonal IgG populations directed against epitopes both within and outside the C2 domain (Prescott, R. et al., supra, 1997; Fulcher, C. A. et al. 1985, "Localization of human factor FVIII inhibitor epitopes to two polypeptide fragments," *Proc. Natl. Acad. Sci. USA* 82:7728–7732). However, some inhibitors are C2-specific and are useful for evaluating the effects of substitution of non-human sequence into the C2 domain (Healey, J. F. et al., 1998, "Residues Glu2181-Val2243 contain a major determinant of the inhibitory epitope in the C2 domain of human factor VIII," *Blood* 92:3701–3709).

C2-specific polyclonal inhibitors from five patients, AA, AJ, HR, LK, RvR (FIG. 3) were used in these studies. A reduction in antigenicity due to mutations at Met2199, Phe2200, and/or Leu2252 always was observed, although individual inhibitors varied in the residues they recognized. Surprisingly, frequently there was a significant increase in Bethesda titer, most notably with the Val2223Ala mutant. The double mutant Met2199Ile/Phe2200Leu exhibited low antigenicity toward all five antibodies, consistent with the fact that the antigenicity of Met2199Ile and/or Phe2200Leu always was reduced. Paradoxically, the double mutant Val2223Ala/Lys2227Glu displayed a reduction in antigenicity toward all five polyclonal antibodies even though in three cases (AA, AJ, and HR) the corresponding individual mutants displayed unchanged or increased antigenicity. The antigenicity of the quadruple mutant Met2199Ile/Phe2200Leu/Val2223Ala/Lys2227Glu was equal or lower than the single or double mutants. The antigenicity of HP20 was the lowest of all the mutants. This is consistent with the existence of antigenic residues in addition to Met2199, Phe2200, and Leu2252 that were not mutated in this study.

Figure 4:
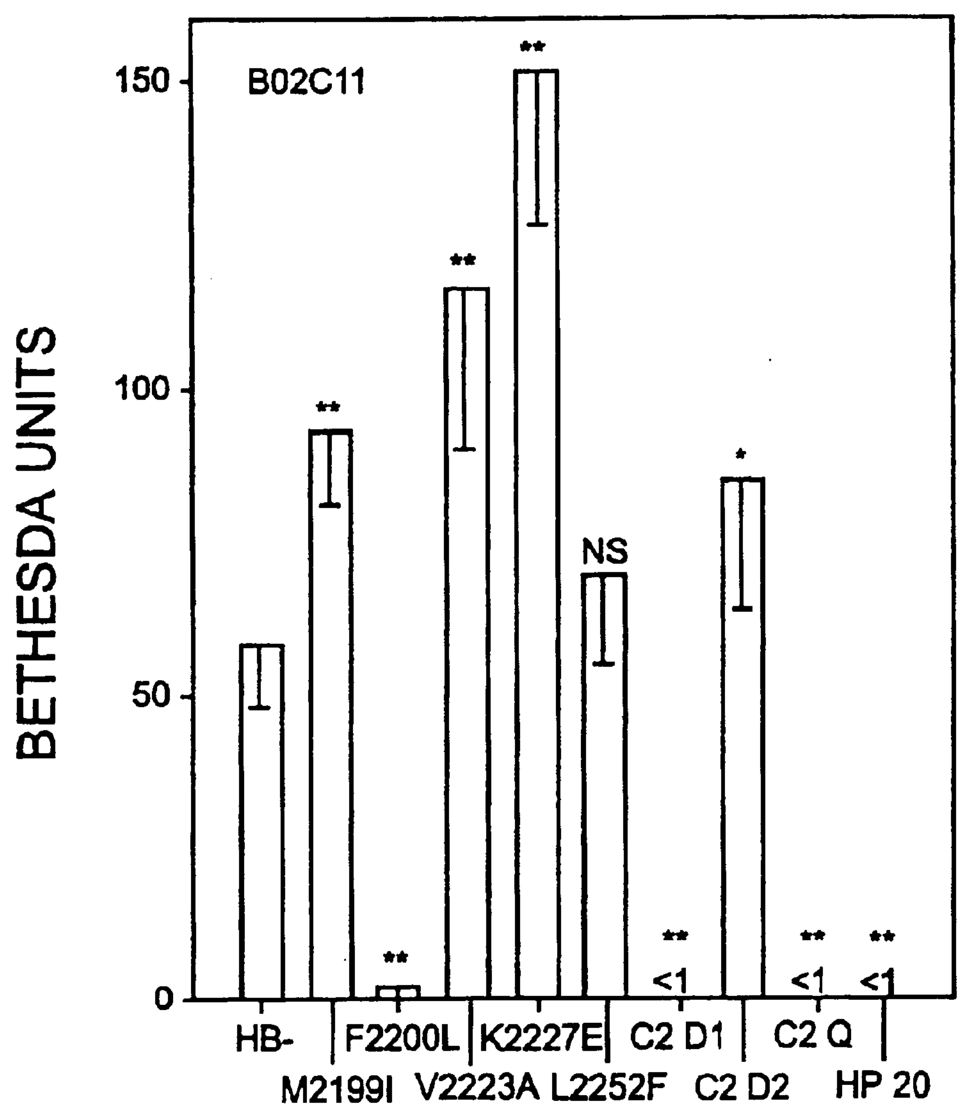
FIG. 4. Bethesda titers of patient monoclonal antibody BO2C11. Abbreviations and notations are as described in FIG. 3 legend.
Figure 5:
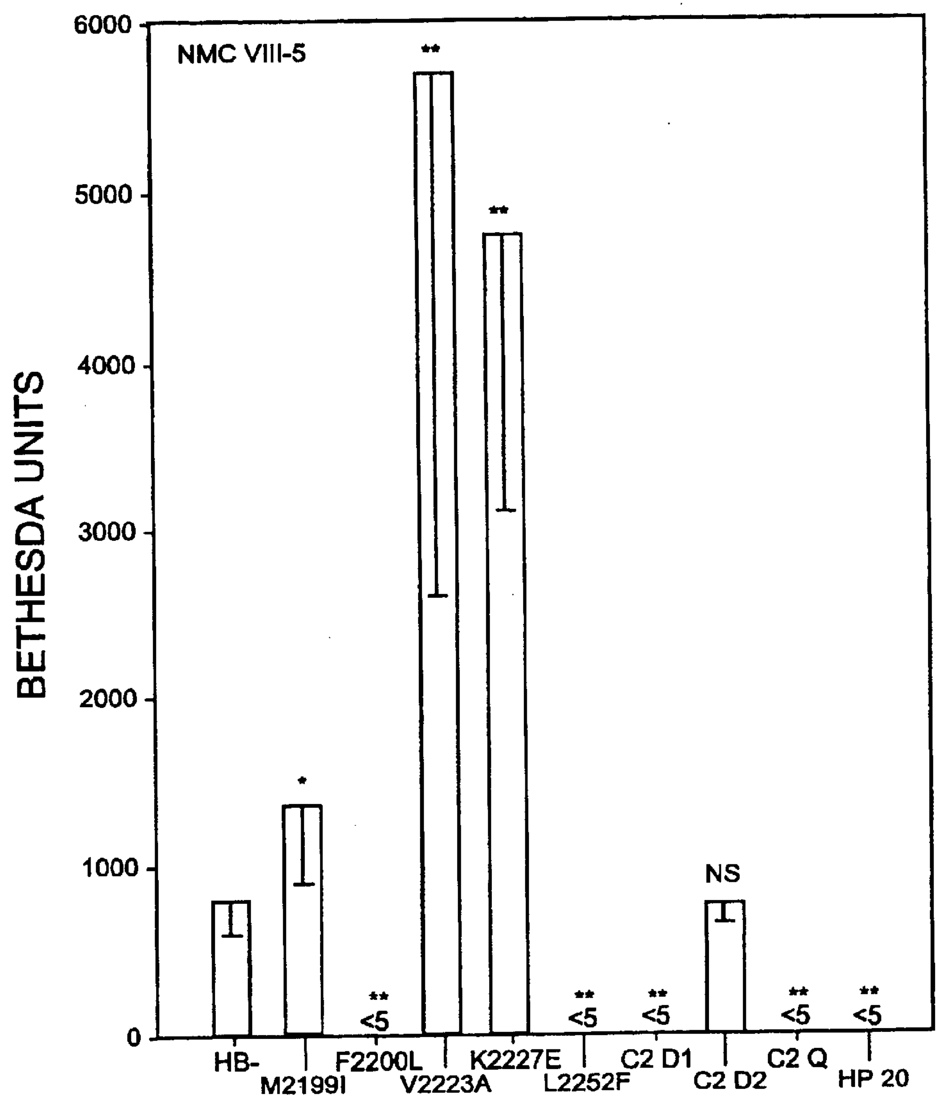
FIG. 5. Bethesda titers of murine monoclonal antibody NMC VIII-5. Abbreviations and notations are as described in FIG. 3 legend

The Bethesda titers of antibodies BO2C11 (Jacquemin, M. G. et al., 1998, "Mechanism and kinetics of factor VIII inactivation: study with an IgG4 monoclonal antibody derived from a hemophilia A patient with inhibitor," *Blood* 92:496–506) and NMC VIII-5 (Shima, M., D. et al., 1993, "A factor VIII neutralizing monoclonal antibody and a human inhibitor alloantibody recognizing epitopes in the C2 domain inhibit factor VIII binding to von Willebrand factor and to phosphatidylserine," *Thromb. Haemost.* 69:240–246) toward HB- and the mutant fVIII molecules are shown in FIGS. 4 and 5, respectively. BO2C11 is a C2-specific human IgG4κ monoclonal antibody derived from transformed B cells of a hemophilia A inhibitor patient. It is the only C2-specific human antibody that has been cloned to date. BO2C11 and NMC VIII-5 both recognize the C2 domain of fVIII and inhibit the binding of fVIII to vWf and phospholipid. NMC VIII-5 can compete for the binding of human polyclonal inhibitors to fVIII. The results with BO2C11 and NMC VIII-5 were similar to those obtained using polyclonal antibody HR (FIG. 3). In all three antibodies, Phe2200 is antigenic, whereas Val2223 and Lys2227 appear to reduce antigenicity.

Mutations at Met2199, Phe2200, and/or Leu2252 were associated with a decrease in antigenicity in most of the seven antibodies tested (Table 1), which was frequently pronounced (FIGS. 3–5). This is consistent with the hypothesis that the Met2199/Phe2200 and Leu2251/Leu2252 loops participate in membrane binding. Even though all seven inhibitors recognized the M2199/Phe2200 loop, the effects of mutations at Met2199 and Phe2200 often differed. For example, Met2199Ile displayed decreased antigenicity and Phe2200Leu displayed increased antigenicity toward antibody AJ, whereas the opposite was true for BO2C11. Thus, the amino acid specificity of AJ and BO2C11 varies, although both recognize the Met2199/Phe2200 loop.

Previously, a series of recombinant hybrid human/porcine FVIII molecules was used to map a major determinant of the C2 epitope(s) to a segment bounded by residues Glu2181-Val2243 (Healey, J. F. et al., 1998, "Residues Glu2181-Val2243 contain a major determinant of the inhibitory epitope in the C2 domain of human factor VIII," *Blood* 92:3701–3709). The Met2199/Phe2200 loop is contained within this region. The Leu2251/Leu2252 loop was neither included nor excluded by this analysis because porcine FVIII also contains leucines at residues 2251 and 2252. Substitution of the entire porcine C2 domain into human fVIII, which produces a molecule designated HP20, is associated with lower antigenicity than the more limited substitutions made in the present study (FIGS. 3–5). This indicates that there are residues outside the Met2199/Phe2200 and Leu2251/Leu2252 loops that contribute to binding by C2 inhibitors.

Recently, X-ray structures of two conformations of the factor V C2 domain in the absence of phospholipid were reported (Macedo-Ribeiro, S. et al., 1999, "Crystal structures of the membrane-binding C2 domain of human coagulation factor V," *Nature* 402:434–439). The authors proposed a model for phospholipid membrane binding that involves a loop containing tryptophans at positions 26 and 27 (human factor V C2 domain numbering), which are homologous to Met2199 and Phe2200 in fVIII. A considerable amount of evidence exists to support the involvement of this loop in phospholipid membrane binding. An inhibitory monoclonal antibody, HV-1 that blocks the binding of factor V to PS maps to this loop (Kim, S. W. et al., 2000, "Identification of functionally important amino acid residues within the C2-domain of human factor V using alanine-scanning mutagenesis" Biochemistry 39:1951–1958; Ortel, T. L. et al., 1994 "Localization of functionally important epitopes within the second C-type domain of coagulation factor V using recombinant chimeras," *J. Biol. Chem.* 269:15898–15905; Ortel, T. L. et al., 1998, "Inhibitory anti-factor V antibodies bind to the factor V C2 domain and are associated with hemorrhagic manifestations," *Blood* 91:4188–4196). Substitution of alanine for residues equivalent to Trp26 and Trp27 in factor Va is associated with decreased binding to PS and loss of coagulant activity (Kim, S. W. et al., supra, 2000, "Identification of functionally important amino acid residues within the C2-domain of human factor V using alanine-scanning mutagenesis," *Biochemistry* 39:1951–1958).

Additionally, a loop containing Leu79, which is homologous to Leu2251 in fVIII, and a loop containing residues Asn41-Asn51, were also proposed to participate in phospholipid membrane binding based on proximity to the Trp26/Trp27 loop (Macedo-Ribeiro, S. et al., 1999, "Crystal structures of the membrane-binding C2 domain of human coagulation factor V," *Nature* 402:434–439). The fVIII segment that is homologous to the Asn41-Asn51loop, His2076-Asn2082, has not been proposed as a phospholipid membrane-binding site (Pratt, K. P., 1999, "Structure of the C2 domain of human factor VIII at 1.5 Å resolution," *Nature* 402:439–442). Conversely, the loop in factor V that is homologous to the Val2223 loop in fVIII was not proposed to participate in phospholipid membrane binding. In the present study, Val2223Ala and Lys2227Glu mutations were usually associated with an increase in antigenicity (Table 1). Thus, these results do not support the hypothesis that these residues participate in phospholipid membrane binding. However, it is possible that they do bind phospholipid but are not frequently targeted by inhibitory antibodies.

The two factor V C2 structures have different conformations, designated "open" and "closed", which are associated with major movements of Trp26 and Trp27 at the phospholipid membrane binding site. These states are proposed to switch the phospholipid membrane binding state to on and off, respectively (Macedo-Ribeiro, S., supra, 1999). The reduction in antigenicity associated with Val2223 and Lys2227 may result because these residues stabilize a similar "closed" conformational state in FVIII that is associated with low affinity membrane and antibody binding. Relaxation of this state by the Val2223Ala and Lys2227Glu mutations would then lead to high affinity antibody binding.

Alternatively, Val2223 and Lys2227 may simply interfere with an antigen-antibody lock-and-key interaction that involves high affinity contacts with other fVIII residues (e.g., Met2199, Phe2200, etc.).

The human C2-specific monoclonal antibody, BO2C11, is important to compare to polyclonal inhibitors because of the heterogeneity that may confound the analysis of the latter. The functional properties of BO2C11 are similar to the murine monoclonal antibody NMC VIII-5. Both antibodies inhibit the binding of fVIII to PS and to vWf and promote dissociation of the fVIII-vWf complex (Jacquemin, M. G. et al., 1998, "Mechanism and kinetics of factor VIII inactivation: study with an IgG4 monoclonal antibody derived from a hemophilia A patient with inhibitor," *Blood* 92:496–506; Shima, M. et al., 1993, "A factor VIII neutralizing monoclonal antibody and a human inhibitor alloantibody recognizing epitopes in the C2 domain inhibit factor VIII binding to von Willebrand factor and to phosphatidylserine," *Thromb.Haemost.* 69:240–246). These results indicate that Phe2200 but not Met2199 is an important part of the epitope recognized by both antibodies (FIGS. 4 and 5). However, NMC VIII-5 recognizes Leu2252 but BO2C11 does not. Val2223 and Lys2227 reduce antigenicity with respect to both antibodies. Thus, BO2C11 and NMC VIII-5 appear to recognize overlapping but not identical epitopes.

The RvR antibody was obtained from a hemophilia A patient who was part of an inhibitor "epidemic" that resulted from exposure to a heat pasteurized FVIII product, CPS-A (Sawamoto, Y. et al., 1998, "C2 domain restricted epitope specificity of inhibitor antibodies elicited by a heat pasteurized product, factor VIII CPS-P, in previously treated hemophilia A patients without inhibitors," *Thromb.Haemostas.* 79:62–68). In 1990 and 1991, several previously treated patients without inhibitors promptly developed C2-specific antibodies after exposure to this product in The Netherlands and Belgium. RvR antibodies block the binding of fVIII to both PS and vWf(Sawamoto, Y. et al., supra, 1998). The RvR epitope maps to the N-terminal, Glu2181-Val2243 region of the fVIII C2 domain recognized by most C2 inhibitors (Healey, J. F. et al., 1998, "Residues Glu2181-Val2243 contain a major determinant of the inhibitory epitope in the C2 domain of human factor VIII," *Blood* 92:3701–3709). The high resolution mapping in the present study indicates that RvR is a typical C2 inhibitor that recognizes primarily the Met2199/Phe2200 and Leu2251/Leu2252 loops. Thus, the immunogenicity associated with the CPS-A appears to be due to enhanced immune recognition of a normal immunodominant epitope rather than to development of a neoepitope.

General Description of Methods

U.S. Pat. No. 5,364,771 described the discovery of hybrid human/porcine factor VIII molecules having coagulant activity, in which elements of the factor VIII molecule of human or pig are substituted for corresponding elements of the factor VIII molecule of the other species. U.S. Pat. No. 5,663,060 describes procoagulant hybrid human/animal and hybrid equivalent factor VIII molecules, in which elements of the factor VIII molecule of one species are substituted for corresponding elements of the factor VIII molecule of the other species.

Since current information indicates that the B domain has no inhibitory epitope and has no known effect on factor VIII function, in some embodiments the B domain is wholly or partially deleted in the active hybrid or hybrid equivalent factor VIII molecules or fragments thereof ("B(−) factor VIII") prepared by any of the methods described herein.

The human factor VIII gene was isolated and expressed in mammalian cells, as reported by Toole, J. J. et al. (1984) *Nature* 312:342–347 (Genetics Institute); Gitschier, J. et al.(1984) *Nature* 312:326–330 (Genentech); Wood, W. I. et al. (1984) *Nature* 312:330–337 (Genentech); Vehar, G. A. et al. (1984) *Nature* 312:337–342 (Genentech); WO 87/04187; WO 88/08035; WO 88/03558; U.S. Pat. No. 4,757,006, and the amino acid sequence was deduced from cDNA. U.S. Pat. No. 4,965,199 to Capon et al. discloses a recombinant DNA method for producing factor VIII in mammalian host cells and purification of human factor VIII. Human factor VIII expression on CHO (Chinese hamster ovary) cells and BHKC (baby hamster kidney cells) has been reported. Human factor VIII has been modified to delete part or all of the B domain (U.S. Pat. No. 4,868,112), and replacement of the human factor VIII B domain with the human factor V B domain has been attempted (U.S. Pat. No. 5,004,803). The cDNA sequence encoding human factor VIII and predicted amino acid sequence are shown in SEQ ID NOs: 1 and 2, respectively. In SEQ ID NO: 1, the coding region begins at nucleotide position 208, the triplet GCC being the codon for amino acid number 1 (Ala) of the mature protein as given in SEQ ID NO: 2.

Porcine factor VIII has been isolated from plasma [Fass, D. N. et al. (1982) *Blood* 59:594]. Partial amino acid sequence of porcine factor VIII corresponding to portions of the N-terminal light chain sequence having homology to ceruloplasmin and coagulation factor V were described by Church et al. (1984) *Proc. Natl. Acad. Sci. USA* 81:6934. Toole, J. J. et al. (1984) *Nature* 312:342–347 described the partial sequencing of the N-terminal end of four amino acid fragments of porcine factor VIII but did not characterize the fragments as to their positions in the factor VIII molecule. The amino acid sequence of the B and part of the A2 domains of porcine factor VIII were reported by Toole, J. J. et al. (1986) *Proc. Natl. Acad. Sci, USA* 83:5939–5942. The CDNA sequence encoding the complete A2 domain of porcine factor VIII and predicted amino acid sequence and hybrid human/porcine factor VIII having substitutions of all domains, all subunits, and specific amino acid sequences were disclosed in U.S. Pat. No. 5,364,771 entitled "Hybrid Human/Porcine factor VIII" issued on Nov. 15, 1994, and in WO 93/20093 published Oct. 14, 1993. The cDNA sequence encoding the A2 domain of porcine factor VIII corresponding to residues 373–740 in mature human factor VIII, as shown in SEQ ID NO: 1, and the predicted amino acid sequence are shown in SEQ ID NOs: 3 and 4, respectively. More recently, the nucleotide and corresponding amino acid sequences of part of the Al domain lacking the first 198 amino acid and of the A2 domain of porcine factor VIII were reported in WO 94/11503, published May 26, 1994. The entire nucleotide sequence encoding porcine factor VIII, including the complete A1 domain, activation peptide, A3, C1 and C2 domains, as well as the encoded amino acid sequence, was finally obtained by Lollar, as disclosed in U.S. Pat. No. 5,859,204, issued Jan. 12, 1999, and in WO 97/49725, published Dec. 31, 1997, both incorporated herein by reference.

Both porcine and human factor VIII are isolated from plasma as a two subunit protein. The subunits, known as the heavy chain and light chain, are held together by a non-covalent bond that requires calcium or other divalent metal ions. The heavy chain of factor VIII contains three domains, A1, A2, and B, which are linked covalently. The light chain of factor VIII also contains three domains, designated A3, C1, and C2. The B domain has no known biological function and can be removed, or partially removed from the molecule proteolytically or by recombinant DNA technology methods without significant alteration in any measurable parameter of factor VIII. Human recombinant factor VIII has a similar structure and function to plasma-derived factor VIII, though it is not glycosylated unless expressed in mammalian cells.

Both human and porcine activated factor VIII ("factor VIIIa") have three subunits due to cleavage of the heavy chain between the A1 and A2 domains. This structure is designated A1/A2/A3-C1-C2. Human factor VIIIa is not stable under the conditions that stabilize porcine factor Villa, presumably because of the weaker association of the A2 subunit of human factor VIIIa. Dissociation of the A2 subunit of human and porcine factor VIIIa is associated with loss of activity in the factor VIIIa molecule. Yakhyaev, A. et al. (1997) *Blood* 90:Suppl. 1, Abstract #126, reported binding of A2 domain by low density lipoprotein receptor-related protein, suggesting that cellular uptake of A2 mediated by such binding acts to down-regulate factor VIII activity.

Expression of "B-domainless factor VIII" is enhanced by including portions of the B-domain. The inclusion of those parts of the B domain designated "SQ" [Lind, P. et al. (1995) supra] was reported to result in favorable expression. "SQ" constructs lack all of the human B domain except for 5 amino acids of the B domain N-terminus and 9 amino acids of the B domain C-terminus.

The purified modified factor VIII or fragment thereof can be assayed for immunoreactivity and coagulation activity by standard assays including, for example, the plasma-free factor VIII assay, the one-stage clotting assay, and the enzyme-linked immunosorbent assay using purified recombinant human factor VIII as a standard.

Other vectors, including both plasmid and eukaryotic viral vectors, may be used to express a recombinant gene construct in eukaryotic cells depending on the preference and judgment of the skilled practitioner (see, for example, Sambrook et al., Chapter 16). Other vectors and expression systems, including bacterial, yeast, and insect cell systems, can be used but are not preferred due to differences in, or lack of, glycosylation.

Recombinant factor VIII protein can be expressed in a variety of cells commonly used for culture and recombinant mammalian protein expression. In particular, a number of rodent cell lines have been found to be especially useful hosts for expression of large proteins. Preferred cell lines, available from the American Type Culture Collection, Rockville, Md., include baby hamster kidney cells, and Chinese hamster ovary (CHO) cells which are cultured using routine procedures and media.

The basis for the greater coagulant activity of porcine factor VIII appears to be the more rapid spontaneous dissociation of the human A2 subunit from human factor VIIIa than the porcine A2 subunit from porcine factor VIIIa. Dissociation of the A2 subunit leads to loss of activity, [Lollar, P. et al. (1990) *J. Biol. Chem.* 265:1688–1692; Lollar, P. et al. (1992) *J. Biol. Chem.* 267:23652–23657; Fay, P. J. et al. (1992) *J. Biol. Chem.* 267:13246–13250].

Factor VIII Molecules with Reduced Immunoreactivity

Epitopes that are immunoreactive with antibodies that inhibit the coagulant activity of factor VIII ("inhibitors" or "inhibitory antibodies") have been characterized based on known structure-function relationships in factor VIII. Presumably, inhibitors could act by disrupting any of the macromolecular interactions associated with the domain structure of factor VIII or its associations with von Willebrand factor, thrombin, factor Xa, factor IXa, or factor X. However, most inhibitory antibodies to human factor VIII act by binding to epitopes located in the 40 kDa A2 domain or 20 kDa C2 domain of factor VIII, disrupting specific functions associated with these domains, as described by Fulcher et al. (1985) *Proc. Natl. Acad. Sci. USA* 82:7728–7732; and Scandella et al. (1988) *Proc. Natl. Acad. Sci. USA* 85:6152–6156. In addition to the A2 and C2 epitopes, there may be a third epitope in the A3 or C1 domain of the light chain of factor VIII, according to Scandella et al. (1993) *Blood* 82:1767–1775. The significance of this putative third epitope is unknown, but it appears to account for a minor fraction of the epitope reactivity in factor VIII.

Anti-A2 antibodies block factor X activation, as shown by Lollar et al. (1994) *J. Clin. Invest.* 93:2497–2504. Previous mapping studies by deletion mutagenesis described by Ware et al. (1992) *Blood Coagul. Fibrinolysis* 3:703–716, located the A2 epitope to within a 20 kDa region of the $NH_2$-terminal end of the 40 kDa A2 domain. Competition immunoradiometric assays have indicated that A2 inhibitors recognize either a common epitope or narrowly clustered epitopes, as described by Scandella et al. (1992) *Throm. Haemostas.* 67:665–671, and as demonstrated in U.S. Pat. No. 5,859,204.

Modified factor VIII molecules can be tested in humans for their reduced antigenicity and/or immunogenicity in clinical trials. In one type of trial, designed to determine whether the factor VIII is immunoreactive with inhibitory antibodies, factor VIII is administered, preferably by intravenous infusion, to approximately 25 patients having factor VIII deficiency who have antibodies that inhibit the coagulant activity of therapeutic human factor VIII. The dosage of the animal or modified animal factor VIII is in a range between 5 and 50 Units/kg body weight, preferably 10–50 Units/kg, and most preferably 40 Units/kg body weight. Approximately 1 hour after each administration, the recovery of factor VIII from blood samples is measured in a one-stage coagulation assay. Samples are taken again approximately 5 hours after infusion, and recovery is measured. Total recovery and the rate of disappearance of factor VIII from the samples is predictive of the antibody titer and inhibitory activity. If the antibody titer is high, factor VIII recovery usually cannot be measured. The recovery results are compared to the recovery results in patients treated with plasma-derived human factor VIII, recombinant human factor VIII, plasma-derived porcine factor VIII, and other commonly used therapeutic forms of factor VIII or factor VIII substitutes.

After identification of clinically significant epitopes, recombinant factor VIII molecules can be expressed that have less than or equal cross-reactivity compared with plasma-derived porcine factor VIII when tested in vitro against a broad survey of inhibitor plasmas. Additional mutagenesis in epitopic regions can be done to reduce cross-reactivity. Reduced cross-reactivity, although desirable, is not necessary to produce a product that may have advantages over the existing plasma-derived porcine factor VIII concentrate, which can produce side effects due to contaminant porcine proteins or contaminant infectious agents such as viruses or prions. A recombinant porcine or modified porcine factor VIII molecule will not contain foreign porcine proteins.

Diagnostic Assays

The factor VIII cDNA and/or protein expressed therefrom, in whole or in part, can be used in assays as diagnostic reagents for the detection of inhibitory antibodies to human or animal factor VIII or modified animal VIII in substrates, including, for example, samples of serum and body fluids of human patients with factor VIII deficiency. These antibody assays include assays such as ELISA assays, immunoblots, radioimmunoassays, immunodiffusion assays, and assay of factor VIII biological activity (e.g., by coagulation assay). Techniques for preparing these reagents and methods for use thereof are known to those skilled in the art. For example, an immunoassay for detection of inhibitory antibodies in a patient serum sample can include reacting the test sample with a sufficient amount of the factor VIII to be tested that a detectable complex can be formed with the inhibitory antibodies in the sample of the test factor VIII is indeed antigenic.

Nucleic acid and amino acid probes can be prepared based on the sequence of the modified factor VIII cDNA or protein molecule or fragments thereof. In some embodiments, these can be labeled using dyes or enzymatic, fluorescent, chemiluminescent, or radioactive labels that are commercially available. The amino acid probes can be used, for example, to screen sera or other body fluids where the presence of inhibitors to human, animal, or hybrid human/animal factor VIII is suspected. Levels of inhibitors can be quantitated in patients and compared to healthy controls, and can be used, for example, to determine whether a patient with a factor VIII deficiency can be treated with an animal or modified animal factor VIII. The cDNA probes can be used, for example, for research purposes in screening DNA libraries.

Preparation of Recombinant Factor VIII

Recombinant factor VIII can be produced through the use of eukaryotic protein expression systems. In general, an eukaryotic cell line, which is deficient in a required gene, is transformed with a vector comprising the gene that it has a deficiency for, and the recombinant DNA which one wishes to express. Transformation can be accomplished by techniques such as electroporation or viral delivery. The cell line chosen to produce the protein is selected to be compatible with the protein of interest, capable of continuously expressing the protein of interests, capable of growing on a medium which facilitates purification of the protein of interest, along with other factors known to those skilled in the art. Examples of such techniques are disclosed in European Patent Application 0 302 968 A2 and U.S. Pat. No. 5,149,637 both of which are incorporated by reference in their entirety.

Testing of Recombinant Factor VIII Molecules

The recombinant factor VIII molecules can be tested in humans for their reduced antigenicity and/or immunogenicity in at least two types of clinical trials. In one type of trial, designed to determine whether the recombinant or recombinant hybrid factor VIII is immunoreactive with inhibitory antibodies, recombinant or recombinant hybrid factor VIII is administered, preferably by intravenous infusion, to approximately 25 patients having factor VIII deficiency who have antibodies to factor VIII that inhibit the coagulant activity of therapeutic human or porcine factor VIII. The dosage of the recombinant or recombinant hybrid factor VIII is in a range between 5 and 50 Units/kg body weight, preferably 10–50 Units/kg, and most preferably 40 Units/kg body weight. Approximately 1 hour after each administration, the recovery of factor VIII from blood samples is measured in a one-stage coagulation assay. Samples are taken again approximately 5 hours after infusion, and recovery is measured. Total recovery and the rate of disappearance of factor VIII from the samples is predictive of the antibody titer and inhibitory activity. If the antibody titer is high, factor VIII recovery usually cannot be measured. The recovery results are compared to the recovery of recovery results in patients treated with plasma-derived human factor VIII, recombinant human factor VIII, porcine factor VIII, and other commonly used therapeutic forms of factor VIII or factor VIII substitutes.

In a second type of clinical trial, designed to determine whether the recombinant or recombinant hybrid factor VIII is immunogenic, i.e., whether patients will develop inhibitory antibodies, recombinant or recombinant hybrid factor VIII is administered, as described in the preceding paragraph, to approximately 100 previously untreated hemophiliac patients who have not developed antibodies to factor VIII. Treatments are given approximately every 2 weeks over a period of 6 months to 1 year. At 1 to 3 month intervals during this period, blood samples are drawn and Bethesda assays or other antibody assays are performed to determine the presence of inhibitory antibodies. Recovery assays can also be done, as described above, after each infusion. Results are compared to hemophiliac patients who receive plasma-derived human factor VIII, recombinant human factor VIII, porcine factor VIII, or other commonly used therapeutic forms of factor VIII or factor VIII substitutes.

Pharmaceutical Compositions

Pharmaceutical compositions comprising recombinant or recombinant hybrid factor VIII, alone or in combination with appropriate pharmaceutical stabilization compounds, delivery vehicles, and/or carrier vehicles, are prepared according to known methods, as described in Remington's *Pharmaceutical Sciences* by E. W. Martin.

In one preferred embodiment, the preferred carriers or delivery vehicles for intravenous infusion are physiological saline or phosphate buffered saline.

In another preferred embodiment, suitable stabilization compounds, delivery vehicles, and carrier vehicles include but are not limited to other human or animal proteins such as albumin.

Phospholipid vesicles or liposomal suspensions are also preferred as pharmaceutically acceptable carriers or delivery vehicles. These can be prepared according to methods known to those skilled in the art and can contain, for example, phosphatidylserine/phosphatidylcholine or other compositions of phospholipids or detergents that together impart a negative charge to the surface, since factor VIII binds to negatively charged phospholipid membranes. Liposomes may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the hybrid factor VIII is then introduced into the container. The container is then swirled by hand to free lipid material from the sides of the container and to disperse lipid aggregates, thereby forming the liposomal suspension.

Recombinant or recombinant hybrid factor VIII can be combined with other suitable stabilization compounds, delivery vehicles, and/or carrier vehicles, including vitamin K dependent clotting factors, tissue factor, and von Willebrand factor (vWf) or a fragment of vWf that contains the factor VIII binding site, and polysaccharides such as sucrose.

Recombinant or recombinant hybrid factor VIII can also be delivered by gene therapy in the same way that human factor VIII can be delivered, using delivery means such as retroviral vectors. This method consists of incorporation of factor VIII cDNA into human cells that are transplanted directly into a factor VIII deficient patient or that are placed in an implantable device, permeable to the factor VIII molecules but impermeable to cells, that is then transplanted. The preferred method will be retroviral-mediated gene transfer. In this method, an exogenous gene (e.g., a factor VIII cDNA) is cloned into the genome of a modified retrovirus. The gene is inserted into the genome of the host cell by viral machinery where it will be expressed by the cell. The retroviral vector is modified so that it will not produce virus, preventing viral infection of the host. The general principles for this type of therapy are known to those skilled in the art and have been reviewed in the literature (e.g., Kohn, D. B. et al. [1989] *Transfusion* 29:812–820).

Recombinant or recombinant hybrid factor VIII can be stored bound to vWf to increase the half-life and shelf-life of the hybrid molecule. Additionally, lyophilization of factor VIII can improve the yields of active molecules in the presence of vWf. Current methods for storage of human and animal factor VIII used by commercial suppliers can be employed for storage of hybrid factor VIII. These methods include: (1) lyophilization of factor VIII in a partially-purified state (as a factor VIII "concentrate" that is infused without further purification); (2) immunoaffinity-purification of factor VIII by the Zimmerman method and lyophilization in the presence of albumin, which stabilizes the factor VIII; (3) lyophilization of recombinant factor VIII in the presence of albumin.

Additionally, hybrid factor VIII has been indefinitely stable at 4° C. in 0.6 M NaCl, 20 mM MES, and 5 mM $CaCl_2$ at pH 6.0 and also can be stored frozen in these buffers and thawed with minimal loss of activity.

Methods of Treatment

Recombinant or recombinant hybrid factor VIII is used to treat uncontrolled bleeding due to factor VIII deficiency (e.g., intraarticular, intracranial, or gastrointestinal hemorrhage) in hemophiliacs with and without inhibitory antibodies and in patients with acquired factor VIII deficiency due to the development of inhibitory antibodies. The active materials are preferably administered intravenously.

Additionally, recombinant or recombinant hybrid factor VIII can be administered by transplant of cells genetically engineered to produce the hybrid or by implantation of a device containing such cells, as described above.

In a preferred embodiment, pharmaceutical compositions of recombinant or recombinant hybrid factor VIII alone or in combination with stabilizers, delivery vehicles, and/or carriers are infused into patients intravenously according to the same procedure that is used for infusion of human or animal factor VIII.

The treatment dosages of recombinant or recombinant hybrid factor VIII composition that must be administered to a patient in need of such treatment will vary depending on the severity of the factor VIII deficiency. Generally, dosage level is adjusted in frequency, duration, and units in keeping with the severity and duration of each patient's bleeding episode. Accordingly, the hybrid factor VIII is included in the pharmaceutically acceptable carrier, delivery vehicle, or stabilizer in an amount sufficient to deliver to a patient a therapeutically effective amount of the hybrid to stop bleeding, as measured by standard clotting assays.

Factor VIII is classically defined as that substance present in normal blood plasma that corrects the clotting defect in plasma derived from individuals with hemophilia A. The coagulant activity in vitro of purified and partially-purified forms offactor VIII is used to calculate the dose offactor VIII for infusions in human patients and is a reliable indicator of activity recovered from patient plasma and of correction of the in vivo bleeding defect. There are no reported discrepancies between standard assay of novel factor VIII molecules in vitro and their behavior in the dog infusion model or in human patients, according to: Lusher, J. M. et al. 328 *New Engl. J. Med.* 328:453–459; Pittman, D. D. et al., (1992)*Blood* 79:389–397; and Brinkhous et al. (1985) *Proc. Natl. Acad. Sci.* 82:8752–8755.

Usually, the desired plasma factor VIII level to be achieved in the patient through administration of the recombinant or recombinant hybrid factor VIII is in the range of 30–100% of normal. In a preferred mode of administration of the recombinant or recombinant hybrid factor VIII, the composition is given intravenously at a preferred dosage in the range from about 5 to 50 units/kg body weight, more preferably in a range of 10–50 units/kg body weight, and most preferably at a dosage of 20–40 units/kg body weight; the interval frequency is in the range from about 8 to 24 hours (in severely affected hemophiliacs); and the duration of treatment in days is in the range from 1 to 10 days or until the bleeding episode is resolved. See, e.g., Roberts, H. R., and M. R. Jones, "Hemophilia and Related Conditions—Congenital Deficiencies of Prothrombin (Factor II, Factor V, and Factors VII to XII)," Ch. 153, 1453–1474, 1460, in *Hematology*, Williams, W. J., et al., ed. (1990). Patients with inhibitors may require more recombinant or recombinant hybrid factor VIII, or patients may require less recombinant or recombinant hybrid factor VIII because of its higher specific activity than human factor VIII or decreased antibody reactivity or immunogenicity. As in treatment with human or porcine factor VIII, the amount of recombinant or recombinant hybrid factor VIII infused is defined by the one-stage factor VIII coagulation assay and, in selected instances, in vivo recovery is determined by measuring the factor VIII in the patient's plasma after infusion. It is to be understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition.

Treatment can take the form of a single intravenous administration of the composition or periodic or continuous administration over an extended period of time, as required. Alternatively, recombinant or recombinant hybrid factor VIII can be administered subcutaneously or orally with liposomes in one or several doses at varying intervals of time.

Factor VIII can also be used to treat uncontrolled bleeding due to factor VIII deficiency in hemophiliacs who have developed antibodies to human factor VIII. In this case, coagulant activity that is superior to that of human or animal factor VIII alone is not necessary. Coagulant activity that is inferior to that of human factor VIII (i.e., less than 3,000 units/mg) will be useful if that activity is not neutralized by antibodies in the patient's plasma.

The recombinant or recombinant hybrid factor VIII molecule and the methods for isolation, characterization, making, and using it generally described above will be further understood with reference to the following non-limiting examples.

EXAMPLES

Materials—Citrated hemophilia A plasma and normal pooled human plasma (FACT) were purchased from George King Biomedical, Inc. (Overland Park, Kans.). Heparin-Sepharose was purchased from Sigma Chemical Co.(St. Louis, Mo.). Fetal bovine serum, geneticin, penicillin, streptomycin, DMEM/F12 medium and AIM-V medium were purchased from Life Technologies, Inc. (Gaithersburg, Md.). Pfu DNA polymerase and the phagemid pBlueScript II KS⁻ were purchased from Stratagene (La Jolla, Calif.). Murine anti-human fVIII monoclonal antibodies ESH4 and ESH8 were purchased from American Diagnostica (Greenwich, Conn.). The murine fVIII C2-specific inhibitory monoclonal antibody NMC VIII-5 was obtained from Dr. Midori Shima, Nara Medical College, Japan. A human fVIII C2-specific IgG4κ monoclonal antibody, BO2C11, which was cloned from a transformed B cell line from patient with hemophilia, was prepared as described previously (Jacquemin, M. G. et al., 1998, "Mechanism and kinetics of factor VIII inactivation: study with an IgG4 monoclonal antibody derived from a hemophilia A patient with inhibitor," *Blood* 92:496–506). Citrated human plasmas from five inhibitor patients, AA, AJ, HR LK, and RvR, were obtained from Dr. Dorothea Scandella. They were used either without further purification (HR, RvR, and AJ) or as IgG preparations (LK and AA). Inhibitor IgG was prepared as described previously (Scandella, D., L. et al., 1992, "A soluble recombinant factor VIII fragment containing the A2 domain binds to some human anti-factor VIII antibodies that are not detected by immunoblotting," *Thromb.Haemostas.* 67:665–671). The inhibitors in HR, LK, AA, and RvR antibodies were specific for the C2 domain as judged by antibody neutralization assays (Prescott, R. et al., 1997, "The inhibitory antibody response is more complex in hemophilia A patients than in most nonhemophiliacs with FVIII autoantibodies," *Blood* 89:3663–3671). AJ was identified as a C2-specific using a panel of recombinant hybrid human/porcine FVIII molecules (Barrow, R. T. et al., 2000, "Reduction of the antigenicity of factor VIII toward complex inhibitory plasmas using multiply-substituted hybrid human/porcine factor VIII molecules," *Blood* 95:557–561). Albumin-free recombinant full-length fVIII was obtained from the Hyland-Immuno Division of Baxter Healthcare (Deerfield, Ill.). Synthetic oligonucleotides were purchased from Life Technologies, Inc. (Gaithersburg, Md.). Restriction enzymes were purchased from New England Biolabs (Beverly, Mass.) or Promega (Madison, Wis.). A cell line derived from baby hamster kidney cells was obtained from Dr. R. T. A. Macgillivray (Funk, W. D. et al., 1990, "Expression of the amino-terminal half-molecule of human serum transferrin in cultured cells and characterization of the recombinant protein," *Biochemistry* 29:1654–1660). A B-domainless fVIII expression vector, designated HB-/ReNeo, containing a NotI site two bases 3' to the stop codon and ampicillin and geneticin resistance genes was prepared as described previously (Healey, J. F. et al., 1998, "Residues Glu2181-Val2243 contain a major determinant of the inhibitory epitope in the C2 domain of human factor VIII," *Blood* 92:3701–3709). HSQ/ReNeo, a human B-domainless fVIII molecule containing a fourteen amino acid segment, SerPheSerGlnAsnProPro ValLeuLysArgHisGlnArg, in place of the B domain in human fVIII (Lind, P. et al., 1995, "Novel forms of B-domain-deleted recombinant factor VIII molecules. Construction and biochemical characterization," *Eur. J. Biochem.* 232:19–27) was constructed by splicing-by-overlap extension (SOE) mutagenesis (Horton, R. M. et al., 1993, "Gene splicing by overlap extension," *Methods Enzymol.* 217:270–279) using HB-/ReNeo as template, essentially as described previously for the corresponding porcine molecule (Healey, J. F. et al., 1998, "Residues Glu2181-Val2243 contain a major determinant of the inhibitory epitope in the C2 domain of human factor VIII," *Blood* 92:3701–3709). HP20, a B-domainless hybrid human/porcine fVIII molecule containing human A1, A2, ap-A3, and C1 domains and the porcine C2 domain was prepared as described previously (Healey, J. F., supra, 1998).

Plasmid DNA was purified using a Qiagen Plasmid Maxi Kit (Qiagen, Inc., Valencia, Calif.). PCR reactions were done using a Hybrid OmniGene thermocycler using Pfu DNA polymerase. PCR products were gel purified, precipitated with ethanol, and ligated into plasmid DNA using T4 DNA ligase (Rapid DNA Ligation Kit, Boehringer Mannheim, Indianapolis, Ind.). Insert-containing plasmids were used to transform *E. coli* Epicurean XL1-Blue cells. All novel fVIII DNA sequences generated by PCR were confirmed by dideoxy sequencing using an Applied Biosystems (Foster City, Calif.) 373a automated DNA sequencer and the PRISM dye terminator kit.

Example 1

Construction of fVIII Mutant cDNAs

Mutations were made in HSQ codons by SOE mutagenesis to produce the following proteins: Met2199Ile (human to porcine), ATG to ATC, Phe2200Leu (human to canine), TTT to TTG, Val2223Ala (human to canine), GTG to GCC, Lys2227Glu (human to porcine), AAA to GAG, Leu2252Phe (human to murine), CTT to TTC, Met2199Ile/Phe2200Leu, ATG to ATC and TTT to TTG, Val2223Ala/Lys2227Glu, GTG to GCC and AAA to GAG, Met2199Ile/Phe2200Leu/Val2223Ala/Lys2227Glu, ATG to ATC, TTT to TTT, GTG to GCC, and AAA to GAG.

HSQ/ReNeo was used as the template in the PCR reactions. The first PCR reaction used the human C1 primer, SEQ ID NO: 3, 5'-GTG GAT TCA TCT GGG ATA AAA CAC-3', designated H3763+, corresponding to nucleotides 3763–3786 in the HSQ sequence, as the sense primer. The following primers were used as antisense primers:

```
Met2199Ile,
5'-AGG AGA CCA GGT GGC AAA GAT ATT GGT AAA GTA GGA TGA-3',        SEQ ID NO:4

Phe2200Leu,
5'-TGA AGG AGA CCA GGT GGC CAA CAT ATT GGT AAA GTA GGA-3',        SEQ ID NO:5

Val2223Ala,
5'-CCA CTC TTT TGG ATT ATT GGC CTG AGG TCT CCA GGC ATT-3',        SEQ ID NO:6

Lys2227Glu,
5'-GTC CAC TTG CAG CCA CTC CTC TGG ATT ATT CAC CTG AGG-3',        SEQ ID NO:7

Leu2252Phe,
5'-CTT CAC ATA CAT GCT GGT GAA CAG AGA TTT TAC TCC CTG-3',        SEQ ID NO:8
```

-continued

```
Met2199Ile/Phe2200Leu,
5'-AGG AGA CCA GGT GGC CAA GAT ATT GGT AAA GTA GGA TGA-3', and     SEQ ID NO:9

Val2223Ala/Lys2227Glu,
5'-CAC TTG CAG CCA CTC CTC TGG ATT ATT GGC CTG AGG TCT CCA GGC-3'. SEQ ID NO:10
```

The second PCR reaction used the ReNeo primer, SEQ ID NO: 11, 5'-AGT TTT TCT ACA ACA GAG GAA GTG-3', designated RE1110-, which is 3' to the C2 domain, as antisense primer. The following primers were used as sense primers:

```
Met2199Ile,
5'-TCA TCC TAC TTT ACC AAT ATC TTT GCC ACC TGG TCT CCT-3',         SEQ ID NO:12

Phe2200Leu,
5'-TCC TAC TTT ACC AAT ATG TTG GCC ACC TGG TCT CCT TGA-3',         SEQ ID NO:13

Val2223Ala,
5'-AAT GCC TGG AGA CCT CAG GCC AAT AAT CCA AAA GAG TGG-3',         SEQ ID NO:14

Lys2227Glu,
5'-CCT CAG GTG AAT AAT CCA GAG GAG TGG CTG CAA GTG GAC-3',         SEQ ID NO:15

Leu2252Phe,
5'-CAG GGA GTA AAA TCT CTG TTC ACC AGC ATG TAT GTG AAG-3',         SEQ ID NO:16

Met2199Ile/Phe2200Leu,
5'-TCA TCC TAC TTT ACC AAT ATC TTG GCC ACC TGG TCT CCT-3', and     SEQ ID NO:17

Val2223Ala/Lys2227Glu,
5'-GCC TGG AGA CCT CAG GCC AAT AAT CCA GAG GAG TGG CTG CAA GTG-3'. SEQ ID NO:18
```

The SOE reaction used fragments from the PCR reactions as templates and H3763+ and RE1110 as primers. The SOE product and HSQ/ReNeo ligation fragments were generated using Swa I and Not I.

The Met2199Ile/Phe2200Leu/Val2223Ala/Lys2227Glu cDNA was constructed as follows. The Met2199Ile/Phe2200Leu cDNA was moved into pBluescript II KS- and digested with Bsu36 I. The Val2223Ala/Lys2227Glu cDNA also was digested with Bsu36 I and the appropriate fragments were ligated. The resulting Met2199Ile/Phe2200Leu/Val2223Ala/Lys2227Glu cDNA was moved into ReNeo by digestion with Swa I and Not I.

Example 2

Expression of Recombinant fVIII Molecules

Transfected cell lines were maintained in Dulbecco's modified Eagle's medium-F12 containing 10% fetal bovine serum, 50 U/ml penicillin, and 50 μg/ml streptomycin. Fetal bovine serum was heat inactivated for one hour at 56° C. before use. Mutant cDNAs in ReNeo were stably transfected into BHK cells, selected for geneticin resistance, switched to serum-free, AIM-V medium for expression, and partially purified by heparin-Sepharose chromatography as described previously (Healey, J. F. et al, supra, 1998).

Example 3

FVIII and fVIII Inhibitor Assays

The activity of recombinant fVIII proteins was measured by one-stage clotting assay (Bowie, E. J. W. and C. A. Owen, 1984, "The clinical and laboratory diagnosis of hemorrhagic disorders," In Disorders of Hemostasis, O. D. Ratnoff and C. D. Forbes, editors. Grune & Stratton, Inc., Orlando, Fla. 43–72). One unit of fVIII is defined as the activity in one ml of normal citrated human plasma. FVIII inhibitor titers were measured by a modification of the Bethesda assay (Kasper, C. K. et al., 1975, "A more uniform measurement of factor VIII inhibitors," *Thromb. Diath. Haemorrh.* 34:869–872) as follows. Recombinant FVIII was added to hemophilia A plasma to a final concentration of 0.8–1.2 units per ml and incubated with varying concentrations of inhibitor for 2 hours at 37° C. To determine the 50% inhibition point that defines the Bethesda unit, dilutions of inhibitor were made that produced residual activities that spanned at least the 35% to 65% range. In some cases, replicate dilutions were made, in which case the average was used. An average of 10 dilutions was made for the determination of each Bethesda titer. Semi-logarithmic plots of percent residual activity versus the log of the reciprocal of the inhibitor dilution appeared linear in all cases. The data were fitted by nonlinear regression using the Marquardt algorithm (SigmaPlot 5.0, SPSS, Inc.) to the equation $$\% \text{ Residual activity} = m(\log x - \log x_{50}) + 50$$

where the fitted parameter $x_{50}$ is the reciprocal dilution that produces 50% inhibition, the fitted parameter m is the slope of the semi-log line and the independent variable x is the reciprocal dilution of the inhibitor sample. The standard error of the estimate (average deviation of data points from the regression line) for 62 Bethesda assays was 10.0±4.0 (mean±1 SD), indicative of the relatively low precision that is inherent in the assay.

The Bethesda titer equals $x_{50}^{-1}$. The estimate of the standard error (SD) of the Bethesda titer was calculated by multiplying the Bethesda titer by the coefficient of variation of $x_{50}$. The Bethesda titers of fVIII mutants and HB- were compared by Student's t test. The mass concentration of fVIII in partially purified preparations was determined by a sandwich ELISA using ESH4 as capture antibody and biotinylated ESH8 as detection antibody as described previously (Lubin, I. M. et al., 1994, "Elimination of a major inhibitor epitope in factor VIII," *J. Biol. Chem.* 269:8639–8641). Full-length recombinant FVIII was used as the standard and values were corrected for the difference in mass between full-length and B-domainless forms of fVIII. Samples were assayed in quadruplicate. The average coefficient of variation was 9.0%. The specific activity of FVIII molecules was calculated by dividing the coagulant activity by the concentration as determined by ELISA. The following values were obtained (units per mg): HB-, 7,800; Met2199Ile, 12,800; Phe2200Leu, 10,200; Val2223Ala, 19,600; Lys2227Glu, 36,200; Leu2252Phe, 10,100; Met2199Ile/Phe2200Leu, 10,000; Val2223Ala/Lys2227Glu, 33,200; Met2199Ile/Phe2200Leu/Val2223Ala/Lys2227Glu, 14,200. The apparent specific activity of some of the mutants is higher than HB-. This may be due to a relatively small decreased ability of the mutants to bind either the capture or detection antibody compared to HB-, leading to an underestimate of fVIII mass and an overestimate of the specific activity.

TABLE 1

Antigenicity of FVIII C2 mutants towards C2-Specific Inhibitory Antibodies Compared to Human FVIII

| Mutant | Antigenicity[a] Less | Equal | More |
|---|---|---|---|
| Met2199Ile | 4/7 | 0/7 | 3/7 |
| Phe2200Leu | 4/7 | 2/7 | 1/7 |
| Val2223Ala | 0/7 | 2/7 | 5/7 |
| Lys2227Glu | 2/7 | 1/7 | 4/7 |
| Leu2252Phe | 4/7 | 3/7 | 0/7 |
| Met2199Ile/Phe2200Leu | 6/7 | 1/7 | 0/7 |
| Val2223Ala/Lys2227Glu | 4/7 | 1/7 | 2/7 |
| Met2199Ile/Phe2200Leu/Val2223Ala/Lys2227Glu | 7/7 | 0/7 | 0/7 |
| HP20 | 7/7 | 0/7 | 0/7 |

[a]Significant difference at the 99% confidence level

What is claimed is:

1. A modified human factor VIII comprising at least one amino acid substitution in the C2 domain wherein the substitution is limited to at least one position selected from the group consisting of 2199, 2200, 2223, 2227, 2251, and 2252 corresponding to SEQ ID NO:2, wherein the modified factor VIII has reduced immunogenicity and/or antigenicity compared to the corresponding human factor VIII protein.

2. The modified human factor VIII of claim 1 lacking a B-domain.

3. The modified human factor VIII of claim 1 wherein one of the substitution is isoleucine substituted for methionine 2199 corresponding to SEQ ID NO:2.

4. The modified human factor VIII of claim 1 wherein one of the substitution is leucine substituted for phenylalanine 2200 corresponding to SEQ ID NO:2.

5. The modified human factor VIII of claim 1 wherein one of the substitution is phenylalanine substituted for leucine 2252 corresponding to SEQ ID NO:2.

6. The modified human factor VIII of claim 1 wherein two of the substitutions are isoleucine substituted for methionine 2199 and leucine substituted for phenylalanine 2200 corresponding to SEQ ID NO:2.

7. The modified human factor VIII of claim 1 wherein two of the substitutions are alanine substituted for valine 2223 and glutamate substituted for lysine 2227 corresponding to SEQ ID NO:2.

8. The modified human factor VIII of claim 1 wherein four of the substitutions are isoleucine substituted for methionine 2199, leucine substituted for phenylalanine 2200, alanine substituted for valine 2223, and glutamate substituted for lysine 2227 corresponding to SEQ ID NO:2.

9. The modified factor of claim 1 which has reduced antigenicity as compared to the corresponding human factor VIII protein.

10. The modified factor of claim 1 which has reduced immunogenicity as compared to the corresponding human factor VIII protein.

11. The modified factor VIII of claim 1 which has reduced immunogenicity and reduced antigenicity as compared to the corresponding human factor VIII protein.

12. The modified factor VIII of claim 1 which has a specific activity greater than about 2,000 units per milligram.

13. The modified factor VIII of claim 1 which has a specific activity greater than about 3,000 units per milligram.

14. The modified factor VIII of claim 1 which has a specific activity greater than about 5,000 units per milligram.

15. The modified factor VIII of claim 1 which has a specific activity greater than about 10,000 units per milligram.

16. The modified factor VIII of claim 1 which is a single mutant.

17. The modified factor VIII of claim 1 which is a double mutant.

18. The modified factor VIII of claim 1 which is a triple mutant.

19. The modified factor VIII of claim 1 which is a quadruple mutant.

20. The modified factor VIII of claim 1 which has lower antigenicity towards at least one C2-specific inhibitory antibody as compared to the corresponding human factor VIII from which the modified factor VIII was derived or full length recombinant factor VIII comprising the amino acid sequence of the corresponding human factor VIII.

21. The modified factor VIII of claim 1 which has an increased or decreased Bethesda titer of monoclonal antibody B02011 as compared to the corresponding human factor VIII from which the modified factor VIII was derived or full length recombinant factor VIII comprising the amino acid sequence of the corresponding human factor VIII.

22. The modified factor VIII of claim 1 which has an increased or decreased Bethesda titer of monoclonal antibody NMC VIII-5 as compared to the corresponding human factor VIII from which the modified factor VIII was derived or full length recombinant factor VIII comprising the amino acid sequence of the corresponding human factor VIII.

23. The modified factor VIII of claim 1 which has an increased or decreased Bethesda titer towards at least one inhibitory antibody preparation as compared to the corresponding human factor VIII from which the modified factor VIII was derived or full length recombinant factor VIII comprising the amino acid sequence of the corresponding human factor VIII.

24. A method for modifying human factor VIII such that reactivity to an inhibitory antibody is reduced and procoagulant activity is retained comprising substituting an amino acid in the C2 domain wherein the substitution is limited to at least one of the amino acids selected from the group consisting of 2199, 2200, 2223, 2227, 2251, and 2252 corresponding to SEQ ID NO:2.

25. The method of claim 24 wherein at least one of the substitutions is at position 2199 corresponding to SEQ ID NO:2.

26. The method of claim 24 wherein at least one of the substitutions is at position 2200 corresponding to SEQ ID NO:2.

27. The method of claim 24 wherein at least one of the substitutions is at position 2223 corresponding to SEQ ID NO:2.

28. The method of claim 24 wherein at least one of the substitutions is position 2227 corresponding to SEQ ID NO:2.

29. The method of claim 24 wherein at least one of the substitutions is position 2252 corresponding to SEQ ID NO:2.

30. The method of claim 24 wherein the modified factor VIII is a single mutant.

31. The method of claim 24 wherein the modified factor VIII is a double mutant.

32. The method of claim 24 wherein the modified factor VIII is a triple mutant.

33. The method of claim 24 wherein the modified factor VIII is a quadruple mutant.

34. A method for modifying human factor VIII such that antigenicity is reduced and procoagulant activity is retained comprising substituting an amino acid in the C2 domain wherein the substitution is limited to at least one of the amino acids at selected from the group consisting of 2199, 2200, 2223, 2227, 2251, and 2252 corresponding to SEQ ID NO:2.

35. The method of claim 34 wherein at least one of the substitutions is at position 2199 corresponding to SEQ ID NO:2.

36. The method of claim 34 wherein at least one of the substitutions is at position 2200 corresponding to SEQ ID NO:2.

37. The method of claim 34 wherein at least one of the substitutions is at position 2223 corresponding to SEQ ID NO:2.

38. The method of claim 34 wherein at least one of the substitutions is at position 2227 corresponding to SEQ ID NO:2.

39. The method of claim 34 wherein at least one of the substitutions is at position 2252 corresponding to SEQ ID NO:2.

40. The method of claim 34 wherein the modified factor VIII is a single mutant.

41. The method of claim 34 wherein the modified factor VIII is a double mutant.

42. The method of claim 34 wherein the modified factor VIII is a triple mutant.

43. The method of claim 34 wherein the modified factor VIII is a quadruple mutant.

* * * * *

UNITED STATES PATENT AND TRADEMARK OFFICE

CERTIFICATE OF CORRECTION

PATENT NO. : 6,770,744 B2
DATED : August 3, 2004
INVENTOR(S) : Lollar

It is certified that error appears in the above-identified patent and that said Letters Patent is hereby corrected as shown below:

Column 5,
Lines 18-19, delete "Met2199Ile/Phe2200Leu/Va2223Ala/Lys2227Glu" and replace with --Met2199Ile/Phe2200Leu/Val2223Ala/Lys2227Glu--.

Column 14,
Line 37, delete "CDNA" and replace with -- cDNA --.

Column 15,
Line 10, delete "factor Villa" and replace with -- factor VIIIa --.

Columns 23 and 24,
In the middle section, delete the nucleotide sequence of SEQ ID NO:13,
"5'-TCC TAC TTT ACC AAT ATG TTG GCC ACC TGG TCT CCT TGA-3" and replace with
--"5'-TCC TAC TTT ACC AAT ATG TTG GCC ACC TGG TCT CCT TCA-3"--.

Signed and Sealed this

Seventh Day of December, 2004

JON W. DUDAS
*Director of the United States Patent and Trademark Office*

SEQUENCE LISTING

```
<160> NUMBER OF SEQ ID NOS: 21

<210> SEQ ID NO 1
<211> LENGTH: 9009
<212> TYPE: DNA
<213> ORGANISM: Homo sapiens
<220> FEATURE:
<221> NAME/KEY: CDS
<222> LOCATION: (208)..(7203)

<400> SEQUENCE: 1

cagtgggtaa gttccttaaa tgctctgcaa agaaattggg acttttcatt aaatcagaaa     60

ttttactttt ttcccctcct gggagctaaa gatattttag agaagaatta accttttgct    120

tctccagttg aacatttgta gcaataagtc atgcaaatag agctctccac ctgcttcttt    180

ctgtgccttt tgcgattctg ctttagt gcc acc aga aga tac tac ctg ggt gca    234
                              Ala Thr Arg Arg Tyr Tyr Leu Gly Ala
                                1               5

gtg gaa ctg tca tgg gac tat atg caa agt gat ctc ggt gag ctg cct      282
Val Glu Leu Ser Trp Asp Tyr Met Gln Ser Asp Leu Gly Glu Leu Pro
 10                  15                  20                  25

gtg gac gca aga ttt cct cct aga gtg cca aaa tct ttt cca ttc aac      330
Val Asp Ala Arg Phe Pro Pro Arg Val Pro Lys Ser Phe Pro Phe Asn
                 30                  35                  40

acc tca gtc gtg tac aaa aag act ctg ttt gta gaa ttc acg gtt cac      378
Thr Ser Val Val Tyr Lys Lys Thr Leu Phe Val Glu Phe Thr Val His
             45                  50                  55

ctt ttc aac atc gct aag cca agg cca ccc tgg atg ggt ctg cta ggt      426
Leu Phe Asn Ile Ala Lys Pro Arg Pro Pro Trp Met Gly Leu Leu Gly
         60                  65                  70

cct acc atc cag gct gag gtt tat gat aca gtg gtc att aca ctt aag      474
Pro Thr Ile Gln Ala Glu Val Tyr Asp Thr Val Val Ile Thr Leu Lys
     75                  80                  85
```

-continued

```
aac atg gct tcc cat cct gtc agt ctt cat gct gtt ggt gta tcc tac      522
Asn Met Ala Ser His Pro Val Ser Leu His Ala Val Gly Val Ser Tyr
 90                  95                 100                 105

tgg aaa gct tct gag gga gct gaa tat gat gat cag acc agt caa agg      570
Trp Lys Ala Ser Glu Gly Ala Glu Tyr Asp Asp Gln Thr Ser Gln Arg
                110                 115                 120

gag aaa gaa gat gat aaa gtc ttc cct ggt gga agc cat aca tat gtc      618
Glu Lys Glu Asp Asp Lys Val Phe Pro Gly Gly Ser His Thr Tyr Val
            125                 130                 135

tgg cag gtc ctg aaa gag aat ggt cca atg gcc tct gac cca ctg tgc      666
Trp Gln Val Leu Lys Glu Asn Gly Pro Met Ala Ser Asp Pro Leu Cys
        140                 145                 150

ctt acc tac tca tat ctt tct cat gtg gac ctg gta aaa gac ttg aat      714
Leu Thr Tyr Ser Tyr Leu Ser His Val Asp Leu Val Lys Asp Leu Asn
    155                 160                 165

tca ggc ctc att gga gcc cta cta gta tgt aga gaa ggg agt ctg gcc      762
Ser Gly Leu Ile Gly Ala Leu Leu Val Cys Arg Glu Gly Ser Leu Ala
170                 175                 180                 185

aag gaa aag aca cag acc ttg cac aaa ttt ata cta ctt ttt gct gta      810
Lys Glu Lys Thr Gln Thr Leu His Lys Phe Ile Leu Leu Phe Ala Val
                190                 195                 200

ttt gat gaa ggg aaa agt tgg cac tca gaa aca aag aac tcc ttg atg      858
Phe Asp Glu Gly Lys Ser Trp His Ser Glu Thr Lys Asn Ser Leu Met
            205                 210                 215

cag gat agg gat gct gca tct gct cgg gcc tgg cct aaa atg cac aca      906
Gln Asp Arg Asp Ala Ala Ser Ala Arg Ala Trp Pro Lys Met His Thr
        220                 225                 230

gtc aat ggt tat gta aac agg tct ctg cca ggt ctg att gga tgc cac      954
Val Asn Gly Tyr Val Asn Arg Ser Leu Pro Gly Leu Ile Gly Cys His
    235                 240                 245

agg aaa tca gtc tat tgg cat gtg att gga atg ggc acc act cct gaa     1002
Arg Lys Ser Val Tyr Trp His Val Ile Gly Met Gly Thr Thr Pro Glu
250                 255                 260                 265

gtg cac tca ata ttc ctc gaa ggt cac aca ttt ctt gtg agg aac cat     1050
Val His Ser Ile Phe Leu Glu Gly His Thr Phe Leu Val Arg Asn His
                270                 275                 280

cgc cag gcg tcc ttg gaa atc tcg cca ata act ttc ctt act gct caa     1098
Arg Gln Ala Ser Leu Glu Ile Ser Pro Ile Thr Phe Leu Thr Ala Gln
            285                 290                 295

aca ctc ttg atg gac ctt gga cag ttt cta ctg ttt tgt cat atc tct     1146
Thr Leu Leu Met Asp Leu Gly Gln Phe Leu Leu Phe Cys His Ile Ser
        300                 305                 310

tcc cac caa cat gat ggc atg gaa gct tat gtc aaa gta gac agc tgt     1194
Ser His Gln His Asp Gly Met Glu Ala Tyr Val Lys Val Asp Ser Cys
    315                 320                 325

cca gag gaa ccc caa cta cga atg aaa aat aat gaa gaa gcg gaa gac     1242
Pro Glu Glu Pro Gln Leu Arg Met Lys Asn Asn Glu Glu Ala Glu Asp
330                 335                 340                 345

tat gat gat gat ctt act gat tct gaa atg gat gtg gtc agg ttt gat     1290
Tyr Asp Asp Asp Leu Thr Asp Ser Glu Met Asp Val Val Arg Phe Asp
                350                 355                 360

gat gac aac tct cct tcc ttt atc caa att cgc tca gtt gcc aag aag     1338
Asp Asp Asn Ser Pro Ser Phe Ile Gln Ile Arg Ser Val Ala Lys Lys
            365                 370                 375

cat cct aaa act tgg gta cat tac att gct gct gaa gag gag gac tgg     1386
His Pro Lys Thr Trp Val His Tyr Ile Ala Ala Glu Glu Glu Asp Trp
        380                 385                 390

gac tat gct ccc tta gtc ctc gcc ccc gat gac aga agt tat aaa agt     1434
Asp Tyr Ala Pro Leu Val Leu Ala Pro Asp Asp Arg Ser Tyr Lys Ser
    395                 400                 405
```

-continued

```
caa tat ttg aac aat ggc cct cag cgg att ggt agg aag tac aaa aaa     1482
Gln Tyr Leu Asn Asn Gly Pro Gln Arg Ile Gly Arg Lys Tyr Lys Lys
410                 415                 420                 425

gtc cga ttt atg gca tac aca gat gaa acc ttt aag act cgt gaa gct     1530
Val Arg Phe Met Ala Tyr Thr Asp Glu Thr Phe Lys Thr Arg Glu Ala
                430                 435                 440

att cag cat gaa tca gga atc ttg gga cct tta ctt tat ggg gaa gtt     1578
Ile Gln His Glu Ser Gly Ile Leu Gly Pro Leu Leu Tyr Gly Glu Val
            445                 450                 455

gga gac aca ctg ttg att ata ttt aag aat caa gca agc aga cca tat     1626
Gly Asp Thr Leu Leu Ile Ile Phe Lys Asn Gln Ala Ser Arg Pro Tyr
        460                 465                 470

aac atc tac cct cac gga atc act gat gtc cgt cct ttg tat tca agg     1674
Asn Ile Tyr Pro His Gly Ile Thr Asp Val Arg Pro Leu Tyr Ser Arg
    475                 480                 485

aga tta cca aaa ggt gta aaa cat ttg aag gat ttt cca att ctg cca     1722
Arg Leu Pro Lys Gly Val Lys His Leu Lys Asp Phe Pro Ile Leu Pro
490                 495                 500                 505

gga gaa ata ttc aaa tat aaa tgg aca gtg act gta gaa gat ggg cca     1770
Gly Glu Ile Phe Lys Tyr Lys Trp Thr Val Thr Val Glu Asp Gly Pro
                510                 515                 520

act aaa tca gat cct cgg tgc ctg acc cgc tat tac tct agt ttc gtt     1818
Thr Lys Ser Asp Pro Arg Cys Leu Thr Arg Tyr Tyr Ser Ser Phe Val
            525                 530                 535

aat atg gag aga gat cta gct tca gga ctc att ggc cct ctc ctc atc     1866
Asn Met Glu Arg Asp Leu Ala Ser Gly Leu Ile Gly Pro Leu Leu Ile
        540                 545                 550

tgc tac aaa gaa tct gta gat caa aga gga aac cag ata atg tca gac     1914
Cys Tyr Lys Glu Ser Val Asp Gln Arg Gly Asn Gln Ile Met Ser Asp
    555                 560                 565

aag agg aat gtc atc ctg ttt tct gta ttt gat gag aac cga agc tgg     1962
Lys Arg Asn Val Ile Leu Phe Ser Val Phe Asp Glu Asn Arg Ser Trp
570                 575                 580                 585

tac ctc aca gag aat ata caa cgc ttt ctc ccc aat cca gct gga gtg     2010
Tyr Leu Thr Glu Asn Ile Gln Arg Phe Leu Pro Asn Pro Ala Gly Val
                590                 595                 600

cag ctt gag gat cca gag ttc caa gcc tcc aac atc atg cac agc atc     2058
Gln Leu Glu Asp Pro Glu Phe Gln Ala Ser Asn Ile Met His Ser Ile
            605                 610                 615

aat ggc tat gtt ttt gat agt ttg cag ttg tca gtt tgt ttg cat gag     2106
Asn Gly Tyr Val Phe Asp Ser Leu Gln Leu Ser Val Cys Leu His Glu
        620                 625                 630

gtg gca tac tgg tac att cta agc att gga gca cag act gac ttc ctt     2154
Val Ala Tyr Trp Tyr Ile Leu Ser Ile Gly Ala Gln Thr Asp Phe Leu
    635                 640                 645

tct gtc ttc ttc tct gga tat acc ttc aaa cac aaa atg gtc tat gaa     2202
Ser Val Phe Phe Ser Gly Tyr Thr Phe Lys His Lys Met Val Tyr Glu
650                 655                 660                 665

gac aca ctc acc cta ttc cca ttc tca gga gaa act gtc ttc atg tcg     2250
Asp Thr Leu Thr Leu Phe Pro Phe Ser Gly Glu Thr Val Phe Met Ser
                670                 675                 680

atg gaa aac cca ggt cta tgg att ctg ggg tgc cac aac tca gac ttt     2298
Met Glu Asn Pro Gly Leu Trp Ile Leu Gly Cys His Asn Ser Asp Phe
            685                 690                 695

cgg aac aga ggc atg acc gcc tta ctg aag gtt tct agt tgt gac aag     2346
Arg Asn Arg Gly Met Thr Ala Leu Leu Lys Val Ser Ser Cys Asp Lys
        700                 705                 710

aac act ggt gat tat tac gag gac agt tat gaa gat att tca gca tac     2394
Asn Thr Gly Asp Tyr Tyr Glu Asp Ser Tyr Glu Asp Ile Ser Ala Tyr
```

-continued

```
    715                 720                 725

ttg ctg agt aaa aac aat gcc att gaa cca aga agc ttc tcc cag aat     2442
Leu Leu Ser Lys Asn Asn Ala Ile Glu Pro Arg Ser Phe Ser Gln Asn
730                 735                 740                 745

tca aga cac cct agc act agg caa aag caa ttt aat gcc acc aca att     2490
Ser Arg His Pro Ser Thr Arg Gln Lys Gln Phe Asn Ala Thr Thr Ile
                750                 755                 760

cca gaa aat gac ata gag aag act gac cct tgg ttt gca cac aga aca     2538
Pro Glu Asn Asp Ile Glu Lys Thr Asp Pro Trp Phe Ala His Arg Thr
            765                 770                 775

cct atg cct aaa ata caa aat gtc tcc tct agt gat ttg ttg atg ctc     2586
Pro Met Pro Lys Ile Gln Asn Val Ser Ser Ser Asp Leu Leu Met Leu
        780                 785                 790

ttg cga cag agt cct act cca cat ggg cta tcc tta tct gat ctc caa     2634
Leu Arg Gln Ser Pro Thr Pro His Gly Leu Ser Leu Ser Asp Leu Gln
    795                 800                 805

gaa gcc aaa tat gag act ttt tct gat gat cca tca cct gga gca ata     2682
Glu Ala Lys Tyr Glu Thr Phe Ser Asp Asp Pro Ser Pro Gly Ala Ile
810                 815                 820                 825

gac agt aat aac agc ctg tct gaa atg aca cac ttc agg cca cag ctc     2730
Asp Ser Asn Asn Ser Leu Ser Glu Met Thr His Phe Arg Pro Gln Leu
                830                 835                 840

cat cac agt ggg gac atg gta ttt acc cct gag tca ggc ctc caa tta     2778
His His Ser Gly Asp Met Val Phe Thr Pro Glu Ser Gly Leu Gln Leu
            845                 850                 855

aga tta aat gag aaa ctg ggg aca act gca gca aca gag ttg aag aaa     2826
Arg Leu Asn Glu Lys Leu Gly Thr Thr Ala Ala Thr Glu Leu Lys Lys
        860                 865                 870

ctt gat ttc aaa gtt tct agt aca tca aat aat ctg att tca aca att     2874
Leu Asp Phe Lys Val Ser Ser Thr Ser Asn Asn Leu Ile Ser Thr Ile
    875                 880                 885

cca tca gac aat ttg gca gca ggt act gat aat aca agt tcc tta gga     2922
Pro Ser Asp Asn Leu Ala Ala Gly Thr Asp Asn Thr Ser Ser Leu Gly
890                 895                 900                 905

ccc cca agt atg cca gtt cat tat gat agt caa tta gat acc act cta     2970
Pro Pro Ser Met Pro Val His Tyr Asp Ser Gln Leu Asp Thr Thr Leu
                910                 915                 920

ttt ggc aaa aag tca tct ccc ctt act gag tct ggt gga cct ctg agc     3018
Phe Gly Lys Lys Ser Ser Pro Leu Thr Glu Ser Gly Gly Pro Leu Ser
            925                 930                 935

ttg agt gaa gaa aat aat gat tca aag ttg tta gaa tca ggt tta atg     3066
Leu Ser Glu Glu Asn Asn Asp Ser Lys Leu Leu Glu Ser Gly Leu Met
        940                 945                 950

aat agc caa gaa agt tca tgg gga aaa aat gta tcg tca aca gag agt     3114
Asn Ser Gln Glu Ser Ser Trp Gly Lys Asn Val Ser Ser Thr Glu Ser
    955                 960                 965

ggt agg tta ttt aaa ggg aaa aga gct cat gga cct gct ttg ttg act     3162
Gly Arg Leu Phe Lys Gly Lys Arg Ala His Gly Pro Ala Leu Leu Thr
970                 975                 980                 985

aaa gat aat gcc tta ttc aaa gtt agc atc tct ttg tta aag aca aac     3210
Lys Asp Asn Ala Leu Phe Lys Val Ser Ile Ser Leu Leu Lys Thr Asn
                990                 995                1000

aaa act tcc aat aat tca gca act aat aga aag act cac att gat ggc     3258
Lys Thr Ser Asn Asn Ser Ala Thr Asn Arg Lys Thr His Ile Asp Gly
           1005                1010                1015

cca tca tta tta att gag aat agt cca tca gtc tgg caa aat ata tta     3306
Pro Ser Leu Leu Ile Glu Asn Ser Pro Ser Val Trp Gln Asn Ile Leu
       1020                1025                1030

gaa agt gac act gag ttt aaa aaa gtg aca cct ttg att cat gac aga     3354
```

-continued

```
Glu Ser Asp Thr Glu Phe Lys Lys Val Thr Pro Leu Ile His Asp Arg
   1035                1040                1045

atg ctt atg gac aaa aat gct aca gct ttg agg cta aat cat atg tca     3402
Met Leu Met Asp Lys Asn Ala Thr Ala Leu Arg Leu Asn His Met Ser
1050                1055                1060                1065

aat aaa act act tca tca aaa aac atg gaa atg gtc caa cag aaa aaa     3450
Asn Lys Thr Thr Ser Ser Lys Asn Met Glu Met Val Gln Gln Lys Lys
               1070                1075                1080

gag ggc ccc att cca cca gat gca caa aat cca gat atg tcg ttc ttt     3498
Glu Gly Pro Ile Pro Pro Asp Ala Gln Asn Pro Asp Met Ser Phe Phe
           1085                1090                1095

aag atg cta ttc ttg cca gaa tca gca agg tgg ata caa agg act cat     3546
Lys Met Leu Phe Leu Pro Glu Ser Ala Arg Trp Ile Gln Arg Thr His
       1100                1105                1110

gga aag aac tct ctg aac tct ggg caa ggc ccc agt cca aag caa tta     3594
Gly Lys Asn Ser Leu Asn Ser Gly Gln Gly Pro Ser Pro Lys Gln Leu
   1115                1120                1125

gta tcc tta gga cca gaa aaa tct gtg gaa ggt cag aat ttc ttg tct     3642
Val Ser Leu Gly Pro Glu Lys Ser Val Glu Gly Gln Asn Phe Leu Ser
1130                1135                1140                1145

gag aaa aac aaa gtg gta gta gga aag ggt gaa ttt aca aag gac gta     3690
Glu Lys Asn Lys Val Val Val Gly Lys Gly Glu Phe Thr Lys Asp Val
               1150                1155                1160

gga ctc aaa gag atg gtt ttt cca agc agc aga aac cta ttt ctt act     3738
Gly Leu Lys Glu Met Val Phe Pro Ser Ser Arg Asn Leu Phe Leu Thr
           1165                1170                1175

aac ttg gat aat tta cat gaa aat aat aca cac aat caa gaa aaa aaa     3786
Asn Leu Asp Asn Leu His Glu Asn Asn Thr His Asn Gln Glu Lys Lys
       1180                1185                1190

att cag gaa gaa ata gaa aag aag gaa aca tta atc caa gag aat gta     3834
Ile Gln Glu Glu Ile Glu Lys Lys Glu Thr Leu Ile Gln Glu Asn Val
   1195                1200                1205

gtt ttg cct cag ata cat aca gtg act ggc act aag aat ttc atg aag     3882
Val Leu Pro Gln Ile His Thr Val Thr Gly Thr Lys Asn Phe Met Lys
1210                1215                1220                1225

aac ctt ttc tta ctg agc act agg caa aat gta gaa ggt tca tat gag     3930
Asn Leu Phe Leu Leu Ser Thr Arg Gln Asn Val Glu Gly Ser Tyr Glu
               1230                1235                1240

ggg gca tat gct cca gta ctt caa gat ttt agg tca tta aat gat tca     3978
Gly Ala Tyr Ala Pro Val Leu Gln Asp Phe Arg Ser Leu Asn Asp Ser
           1245                1250                1255

aca aat aga aca aag aaa cac aca gct cat ttc tca aaa aaa ggg gag     4026
Thr Asn Arg Thr Lys Lys His Thr Ala His Phe Ser Lys Lys Gly Glu
       1260                1265                1270

gaa gaa aac ttg gaa ggc ttg gga aat caa acc aag caa att gta gag     4074
Glu Glu Asn Leu Glu Gly Leu Gly Asn Gln Thr Lys Gln Ile Val Glu
   1275                1280                1285

aaa tat gca tgc acc aca agg ata tct cct aat aca agc cag cag aat     4122
Lys Tyr Ala Cys Thr Thr Arg Ile Ser Pro Asn Thr Ser Gln Gln Asn
1290                1295                1300                1305

ttt gtc acg caa cgt agt aag aga gct ttg aaa caa ttc aga ctc cca     4170
Phe Val Thr Gln Arg Ser Lys Arg Ala Leu Lys Gln Phe Arg Leu Pro
               1310                1315                1320

cta gaa gaa aca gaa ctt gaa aaa agg ata att gtg gat gac acc tca     4218
Leu Glu Glu Thr Glu Leu Glu Lys Arg Ile Ile Val Asp Asp Thr Ser
           1325                1330                1335

acc cag tgg tcc aaa aac atg aaa cat ttg acc ccg agc acc ctc aca     4266
Thr Gln Trp Ser Lys Asn Met Lys His Leu Thr Pro Ser Thr Leu Thr
       1340                1345                1350
```

-continued

```
cag ata gac tac aat gag aag gag aaa ggg gcc att act cag tct ccc     4314
Gln Ile Asp Tyr Asn Glu Lys Glu Lys Gly Ala Ile Thr Gln Ser Pro
   1355                1360                1365

tta tca gat tgc ctt acg agg agt cat agc atc cct caa gca aat aga     4362
Leu Ser Asp Cys Leu Thr Arg Ser His Ser Ile Pro Gln Ala Asn Arg
1370                1375                1380                1385

tct cca tta ccc att gca aag gta tca tca ttt cca tct att aga cct     4410
Ser Pro Leu Pro Ile Ala Lys Val Ser Ser Phe Pro Ser Ile Arg Pro
               1390                1395                1400

ata tat ctg acc agg gtc cta ttc caa gac aac tct tct cat ctt cca     4458
Ile Tyr Leu Thr Arg Val Leu Phe Gln Asp Asn Ser Ser His Leu Pro
           1405                1410                1415

gca gca tct tat aga aag aaa gat tct ggg gtc caa gaa agc agt cat     4506
Ala Ala Ser Tyr Arg Lys Lys Asp Ser Gly Val Gln Glu Ser Ser His
       1420                1425                1430

ttc tta caa gga gcc aaa aaa aat aac ctt tct tta gcc att cta acc     4554
Phe Leu Gln Gly Ala Lys Lys Asn Asn Leu Ser Leu Ala Ile Leu Thr
   1435                1440                1445

ttg gag atg act ggt gat caa aga gag gtt ggc tcc ctg ggg aca agt     4602
Leu Glu Met Thr Gly Asp Gln Arg Glu Val Gly Ser Leu Gly Thr Ser
1450                1455                1460                1465

gcc aca aat tca gtc aca tac aag aaa gtt gag aac act gtt ctc ccg     4650
Ala Thr Asn Ser Val Thr Tyr Lys Lys Val Glu Asn Thr Val Leu Pro
               1470                1475                1480

aaa cca gac ttg ccc aaa aca tct ggc aaa gtt gaa ttg ctt cca aaa     4698
Lys Pro Asp Leu Pro Lys Thr Ser Gly Lys Val Glu Leu Leu Pro Lys
           1485                1490                1495

gtt cac att tat cag aag gac cta ttc cct acg gaa act agc aat ggg     4746
Val His Ile Tyr Gln Lys Asp Leu Phe Pro Thr Glu Thr Ser Asn Gly
       1500                1505                1510

tct cct ggc cat ctg gat ctc gtg gaa ggg agc ctt ctt cag gga aca     4794
Ser Pro Gly His Leu Asp Leu Val Glu Gly Ser Leu Leu Gln Gly Thr
   1515                1520                1525

gag gga gcg att aag tgg aat gaa gca aac aga cct gga aaa gtt ccc     4842
Glu Gly Ala Ile Lys Trp Asn Glu Ala Asn Arg Pro Gly Lys Val Pro
1530                1535                1540                1545

ttt ctg aga gta gca aca gaa agc tct gca aag act ccc tcc aag cta     4890
Phe Leu Arg Val Ala Thr Glu Ser Ser Ala Lys Thr Pro Ser Lys Leu
               1550                1555                1560

ttg gat cct ctt gct tgg gat aac cac tat ggt act cag ata cca aaa     4938
Leu Asp Pro Leu Ala Trp Asp Asn His Tyr Gly Thr Gln Ile Pro Lys
           1565                1570                1575

gaa gag tgg aaa tcc caa gag aag tca cca gaa aaa aca gct ttt aag     4986
Glu Glu Trp Lys Ser Gln Glu Lys Ser Pro Glu Lys Thr Ala Phe Lys
       1580                1585                1590

aaa aag gat acc att ttg tcc ctg aac gct tgt gaa agc aat cat gca     5034
Lys Lys Asp Thr Ile Leu Ser Leu Asn Ala Cys Glu Ser Asn His Ala
   1595                1600                1605

ata gca gca ata aat gag gga caa aat aag ccc gaa ata gaa gtc acc     5082
Ile Ala Ala Ile Asn Glu Gly Gln Asn Lys Pro Glu Ile Glu Val Thr
1610                1615                1620                1625

tgg gca aag caa ggt agg act gaa agg ctg tgc tct caa aac cca cca     5130
Trp Ala Lys Gln Gly Arg Thr Glu Arg Leu Cys Ser Gln Asn Pro Pro
               1630                1635                1640

gtc ttg aaa cgc cat caa cgg gaa ata act cgt act act ctt cag tca     5178
Val Leu Lys Arg His Gln Arg Glu Ile Thr Arg Thr Thr Leu Gln Ser
           1645                1650                1655

gat caa gag gaa att gac tat gat gat acc ata tca gtt gaa atg aag     5226
Asp Gln Glu Glu Ile Asp Tyr Asp Asp Thr Ile Ser Val Glu Met Lys
       1660                1665                1670
```

-continued

```
aag gaa gat ttt gac att tat gat gag gat gaa aat cag agc ccc cgc     5274
Lys Glu Asp Phe Asp Ile Tyr Asp Glu Asp Glu Asn Gln Ser Pro Arg
   1675                1680                1685

agc ttt caa aag aaa aca cga cac tat ttt att gct gca gtg gag agg     5322
Ser Phe Gln Lys Lys Thr Arg His Tyr Phe Ile Ala Ala Val Glu Arg
1690                1695                1700                1705

ctc tgg gat tat ggg atg agt agc tcc cca cat gtt cta aga aac agg     5370
Leu Trp Asp Tyr Gly Met Ser Ser Ser Pro His Val Leu Arg Asn Arg
               1710                1715                1720

gct cag agt ggc agt gtc cct cag ttc aag aaa gtt gtt ttc cag gaa     5418
Ala Gln Ser Gly Ser Val Pro Gln Phe Lys Lys Val Val Phe Gln Glu
           1725                1730                1735

ttt act gat ggc tcc ttt act cag ccc tta tac cgt gga gaa cta aat     5466
Phe Thr Asp Gly Ser Phe Thr Gln Pro Leu Tyr Arg Gly Glu Leu Asn
       1740                1745                1750

gaa cat ttg gga ctc ctg ggg cca tat ata aga gca gaa gtt gaa gat     5514
Glu His Leu Gly Leu Leu Gly Pro Tyr Ile Arg Ala Glu Val Glu Asp
   1755                1760                1765

aat atc atg gta act ttc aga aat cag gcc tct cgt ccc tat tcc ttc     5562
Asn Ile Met Val Thr Phe Arg Asn Gln Ala Ser Arg Pro Tyr Ser Phe
1770                1775                1780                1785

tat tct agc ctt att tct tat gag gaa gat cag agg caa gga gca gaa     5610
Tyr Ser Ser Leu Ile Ser Tyr Glu Glu Asp Gln Arg Gln Gly Ala Glu
               1790                1795                1800

cct aga aaa aac ttt gtc aag cct aat gaa acc aaa act tac ttt tgg     5658
Pro Arg Lys Asn Phe Val Lys Pro Asn Glu Thr Lys Thr Tyr Phe Trp
           1805                1810                1815

aaa gtg caa cat cat atg gca ccc act aaa gat gag ttt gac tgc aaa     5706
Lys Val Gln His His Met Ala Pro Thr Lys Asp Glu Phe Asp Cys Lys
       1820                1825                1830

gcc tgg gct tat ttc tct gat gtt gac ctg gaa aaa gat gtg cac tca     5754
Ala Trp Ala Tyr Phe Ser Asp Val Asp Leu Glu Lys Asp Val His Ser
   1835                1840                1845

ggc ctg att gga ccc ctt ctg gtc tgc cac act aac aca ctg aac cct     5802
Gly Leu Ile Gly Pro Leu Leu Val Cys His Thr Asn Thr Leu Asn Pro
1850                1855                1860                1865

gct cat ggg aga caa gtg aca gta cag gaa ttt gct ctg ttt ttc acc     5850
Ala His Gly Arg Gln Val Thr Val Gln Glu Phe Ala Leu Phe Phe Thr
               1870                1875                1880

atc ttt gat gag acc aaa agc tgg tac ttc act gaa aat atg gaa aga     5898
Ile Phe Asp Glu Thr Lys Ser Trp Tyr Phe Thr Glu Asn Met Glu Arg
           1885                1890                1895

aac tgc agg gct ccc tgc aat atc cag atg gaa gat ccc act ttt aaa     5946
Asn Cys Arg Ala Pro Cys Asn Ile Gln Met Glu Asp Pro Thr Phe Lys
       1900                1905                1910

gag aat tat cgc ttc cat gca atc aat ggc tac ata atg gat aca cta     5994
Glu Asn Tyr Arg Phe His Ala Ile Asn Gly Tyr Ile Met Asp Thr Leu
   1915                1920                1925

cct ggc tta gta atg gct cag gat caa agg att cga tgg tat ctg ctc     6042
Pro Gly Leu Val Met Ala Gln Asp Gln Arg Ile Arg Trp Tyr Leu Leu
1930                1935                1940                1945

agc atg ggc agc aat gaa aac atc cat tct att cat ttc agt gga cat     6090
Ser Met Gly Ser Asn Glu Asn Ile His Ser Ile His Phe Ser Gly His
               1950                1955                1960

gtg ttc act gta cga aaa aaa gag gag tat aaa atg gca ctg tac aat     6138
Val Phe Thr Val Arg Lys Lys Glu Glu Tyr Lys Met Ala Leu Tyr Asn
           1965                1970                1975

ctc tat cca ggt gtt ttt gag aca gtg gaa atg tta cca tcc aaa gct     6186
Leu Tyr Pro Gly Val Phe Glu Thr Val Glu Met Leu Pro Ser Lys Ala
```

-continued

```
      1980                1985                1990

gga att tgg cgg gtg gaa tgc ctt att ggc gag cat cta cat gct ggg     6234
Gly Ile Trp Arg Val Glu Cys Leu Ile Gly Glu His Leu His Ala Gly
   1995                2000                2005

atg agc aca ctt ttt ctg gtg tac agc aat aag tgt cag act ccc ctg     6282
Met Ser Thr Leu Phe Leu Val Tyr Ser Asn Lys Cys Gln Thr Pro Leu
2010                2015                2020                2025

gga atg gct tct gga cac att aga gat ttt cag att aca gct tca gga     6330
Gly Met Ala Ser Gly His Ile Arg Asp Phe Gln Ile Thr Ala Ser Gly
               2030                2035                2040

caa tat gga cag tgg gcc cca aag ctg gcc aga ctt cat tat tcc gga     6378
Gln Tyr Gly Gln Trp Ala Pro Lys Leu Ala Arg Leu His Tyr Ser Gly
           2045                2050                2055

tca atc aat gcc tgg agc acc aag gag ccc ttt tct tgg atc aag gtg     6426
Ser Ile Asn Ala Trp Ser Thr Lys Glu Pro Phe Ser Trp Ile Lys Val
       2060                2065                2070

gat ctg ttg gca cca atg att att cac ggc atc aag acc cag ggt gcc     6474
Asp Leu Leu Ala Pro Met Ile Ile His Gly Ile Lys Thr Gln Gly Ala
   2075                2080                2085

cgt cag aag ttc tcc agc ctc tac atc tct cag ttt atc atc atg tat     6522
Arg Gln Lys Phe Ser Ser Leu Tyr Ile Ser Gln Phe Ile Ile Met Tyr
2090                2095                2100                2105

agt ctt gat ggg aag aag tgg cag act tat cga gga aat tcc act gga     6570
Ser Leu Asp Gly Lys Lys Trp Gln Thr Tyr Arg Gly Asn Ser Thr Gly
               2110                2115                2120

acc tta atg gtc ttc ttt ggc aat gtg gat tca tct ggg ata aaa cac     6618
Thr Leu Met Val Phe Phe Gly Asn Val Asp Ser Ser Gly Ile Lys His
           2125                2130                2135

aat att ttt aac cct cca att att gct cga tac atc cgt ttg cac cca     6666
Asn Ile Phe Asn Pro Pro Ile Ile Ala Arg Tyr Ile Arg Leu His Pro
       2140                2145                2150

act cat tat agc att cgc agc act ctt cgc atg gag ttg atg ggc tgt     6714
Thr His Tyr Ser Ile Arg Ser Thr Leu Arg Met Glu Leu Met Gly Cys
   2155                2160                2165

gat tta aat agt tgc agc atg cca ttg gga atg gag agt aaa gca ata     6762
Asp Leu Asn Ser Cys Ser Met Pro Leu Gly Met Glu Ser Lys Ala Ile
2170                2175                2180                2185

tca gat gca cag att act gct tca tcc tac ttt acc aat atg ttt gcc     6810
Ser Asp Ala Gln Ile Thr Ala Ser Ser Tyr Phe Thr Asn Met Phe Ala
               2190                2195                2200

acc tgg tct cct tca aaa gct cga ctt cac ctc caa ggg agg agt aat     6858
Thr Trp Ser Pro Ser Lys Ala Arg Leu His Leu Gln Gly Arg Ser Asn
           2205                2210                2215

gcc tgg aga cct cag gtg aat aat cca aaa gag tgg ctg caa gtg gac     6906
Ala Trp Arg Pro Gln Val Asn Asn Pro Lys Glu Trp Leu Gln Val Asp
       2220                2225                2230

ttc cag aag aca atg aaa gtc aca gga gta act act cag gga gta aaa     6954
Phe Gln Lys Thr Met Lys Val Thr Gly Val Thr Thr Gln Gly Val Lys
   2235                2240                2245

tct ctg ctt acc agc atg tat gtg aag gag ttc ctc atc tcc agc agt     7002
Ser Leu Leu Thr Ser Met Tyr Val Lys Glu Phe Leu Ile Ser Ser Ser
2250                2255                2260                2265

caa gat ggc cat cag tgg act ctc ttt ttt cag aat ggc aaa gta aag     7050
Gln Asp Gly His Gln Trp Thr Leu Phe Phe Gln Asn Gly Lys Val Lys
               2270                2275                2280

gtt ttt cag gga aat caa gac tcc ttc aca cct gtg gtg aac tct cta     7098
Val Phe Gln Gly Asn Gln Asp Ser Phe Thr Pro Val Val Asn Ser Leu
           2285                2290                2295

gac cca ccg tta ctg act cgc tac ctt cga att cac ccc cag agt tgg     7146
```

-continued

```
Asp Pro Pro Leu Leu Thr Arg Tyr Leu Arg Ile His Pro Gln Ser Trp
       2300                2305                2310

gtg cac cag att gcc ctg agg atg gag gtt ctg ggc tgc gag gca cag     7194
Val His Gln Ile Ala Leu Arg Met Glu Val Leu Gly Cys Glu Ala Gln
   2315                2320                2325

gac ctc tac tgagggtggc cactgcagca cctgccactg ccgtcacctc             7243
Asp Leu Tyr
2330

tccctcctca gctccagggc agtgtccctc cctggcttgc cttctacctt tgtgctaaat   7303

cctagcagac actgccttga agcctcctga attaactatc atcagtcctg catttctttg   7363

gtgggggcc aggagggtgc atccaattta acttaactct tacctatttt ctgcagctgc    7423

tcccagatta ctccttcctt ccaatataac taggcaaaaa gaagtgagga gaaacctgca   7483

tgaaagcatt cttccctgaa aagttaggcc tctcagagtc accacttcct ctgttgtaga   7543

aaaactatgt gatgaaactt tgaaaaagat atttatgatg ttaacatttc aggttaagcc   7603

tcatacgttt aaaataaaac tctcagttgt ttattatcct gatcaagcat ggaacaaagc   7663

atgtttcagg atcagatcaa tacaatcttg gagtcaaaag gcaaatcatt tggacaatct   7723

gcaaaatgga gagaatacaa taactactac agtaaagtct gtttctgctt ccttacacat   7783

agatataatt atgttattta gtcattatga ggggcacatt cttatctcca aaactagcat   7843

tcttaaactg agaattatag atggggttca agaatcccta agtcccctga aattatataa   7903

ggcattctgt ataaatgcaa atgtgcattt ttctgacgag tgtccataga tataaagcca   7963

ttggtcttaa ttctgaccaa taaaaaaata agtcaggagg atgcaattgt tgaaagcttt   8023

gaaataaaat aacatgtctt cttgaaattt gtgatggcca agaaagaaaa tgatgatgac   8083

attaggcttc taaaggacat acatttaata tttctgtgga aatatgagga aaatccatgg   8143

ttatctgaga taggagatac aaactttgta attctaataa tgcactcagt ttactctctc   8203

cctctactaa tttcctgctg aaaataacac aacaaaaatg taacagggga aattatatac   8263

cgtgactgaa aactagagtc ctacttacat agttgaaata tcaaggaggt cagaagaaaa   8323

ttggactggt gaaaacagaa aaaacactcc agtctgccat atcaccacac aataggatcc   8383

cccttcttgc cctccacccc cataagattg tgaagggttt actgctcctt ccatctgcct   8443

gcacccccttc actatgacta cacagaactc tcctgatagt aaagggggct ggaggcaagg  8503

ataagttata gagcagttgg aggaagcatc caaagactgc aacccagggc aaatggaaaa   8563

caggagatcc taatatgaaa gaaaaatgga tcccaatctg agaaaaggca aaagaatggc   8623

tactttttc tatgctggag tattttctaa taatcctgct tgacccttat ctgacctctt    8683

tggaaactat aacatagctg tcacagtata gtcacaatcc acaaatgatg caggtgcaaa   8743

tggtttatag ccctgtgaag ttcttaaagt ttagaggcta acttacagaa atgaataagt   8803

tgttttgttt tatagcccgg tagaggagtt aaccccaaag gtgatatggt tttatttcct   8863

gttatgttta acttgataat cttattttgg cattcttttc ccattgacta tatacatctc   8923

tatttctcaa atgttcatgg aactagctct tttattttcc tgctggtttc ttcagtaatg   8983

agttaaataa aacattgaca cataca                                        9009
```

<210> SEQ ID NO 2
<211> LENGTH: 2332
<212> TYPE: PRT
<213> ORGANISM: Homo sapiens

<400> SEQUENCE: 2

-continued

```
Ala Thr Arg Arg Tyr Tyr Leu Gly Ala Val Glu Leu Ser Trp Asp Tyr
  1               5                  10                  15

Met Gln Ser Asp Leu Gly Glu Leu Pro Val Asp Ala Arg Phe Pro Pro
             20                  25                  30

Arg Val Pro Lys Ser Phe Pro Phe Asn Thr Ser Val Val Tyr Lys Lys
         35                  40                  45

Thr Leu Phe Val Glu Phe Thr Val His Leu Phe Asn Ile Ala Lys Pro
     50                  55                  60

Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
```

-continued

```
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
    770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
        835                 840                 845
```

-continued

```
Phe Thr Pro Glu Ser Gly Leu Gln Leu Arg Leu Asn Glu Lys Leu Gly
    850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
        995                 1000                1005

Thr Asn Arg Lys Thr His Ile Asp Gly Pro Ser Leu Leu Ile Glu Asn
   1010                 1015                1020

Ser Pro Ser Val Trp Gln Asn Ile Leu Glu Ser Asp Thr Glu Phe Lys
1025                1030                1035                1040

Lys Val Thr Pro Leu Ile His Asp Arg Met Leu Met Asp Lys Asn Ala
                1045                1050                1055

Thr Ala Leu Arg Leu Asn His Met Ser Asn Lys Thr Thr Ser Ser Lys
           1060                 1065                1070

Asn Met Glu Met Val Gln Gln Lys Lys Glu Gly Pro Ile Pro Pro Asp
       1075                 1080                1085

Ala Gln Asn Pro Asp Met Ser Phe Phe Lys Met Leu Phe Leu Pro Glu
   1090                 1095                1100

Ser Ala Arg Trp Ile Gln Arg Thr His Gly Lys Asn Ser Leu Asn Ser
1105                1110                1115                1120

Gly Gln Gly Pro Ser Pro Lys Gln Leu Val Ser Leu Gly Pro Glu Lys
                1125                1130                1135

Ser Val Glu Gly Gln Asn Phe Leu Ser Glu Lys Asn Lys Val Val Val
           1140                 1145                1150

Gly Lys Gly Glu Phe Thr Lys Asp Val Gly Leu Lys Glu Met Val Phe
       1155                 1160                1165

Pro Ser Ser Arg Asn Leu Phe Leu Thr Asn Leu Asp Asn Leu His Glu
   1170                 1175                1180

Asn Asn Thr His Asn Gln Glu Lys Lys Ile Gln Glu Glu Ile Glu Lys
1185                1190                1195                1200

Lys Glu Thr Leu Ile Gln Glu Asn Val Val Leu Pro Gln Ile His Thr
                1205                1210                1215

Val Thr Gly Thr Lys Asn Phe Met Lys Asn Leu Phe Leu Leu Ser Thr
           1220                 1225                1230

Arg Gln Asn Val Glu Gly Ser Tyr Glu Gly Ala Tyr Ala Pro Val Leu
       1235                 1240                1245

Gln Asp Phe Arg Ser Leu Asn Asp Ser Thr Asn Arg Thr Lys Lys His
   1250                 1255                1260
```

-continued

```
Thr Ala His Phe Ser Lys Lys Gly Glu Glu Glu Asn Leu Glu Gly Leu
1265                1270                1275                1280

Gly Asn Gln Thr Lys Gln Ile Val Glu Lys Tyr Ala Cys Thr Thr Arg
               1285                1290                1295

Ile Ser Pro Asn Thr Ser Gln Gln Asn Phe Val Thr Gln Arg Ser Lys
           1300                1305                1310

Arg Ala Leu Lys Gln Phe Arg Leu Pro Leu Glu Glu Thr Glu Leu Glu
       1315                1320                1325

Lys Arg Ile Ile Val Asp Asp Thr Ser Thr Gln Trp Ser Lys Asn Met
   1330                1335                1340

Lys His Leu Thr Pro Ser Thr Leu Thr Gln Ile Asp Tyr Asn Glu Lys
1345                1350                1355                1360

Glu Lys Gly Ala Ile Thr Gln Ser Pro Leu Ser Asp Cys Leu Thr Arg
               1365                1370                1375

Ser His Ser Ile Pro Gln Ala Asn Arg Ser Pro Leu Pro Ile Ala Lys
           1380                1385                1390

Val Ser Ser Phe Pro Ser Ile Arg Pro Ile Tyr Leu Thr Arg Val Leu
       1395                1400                1405

Phe Gln Asp Asn Ser Ser His Leu Pro Ala Ala Ser Tyr Arg Lys Lys
   1410                1415                1420

Asp Ser Gly Val Gln Glu Ser Ser His Phe Leu Gln Gly Ala Lys Lys
1425                1430                1435                1440

Asn Asn Leu Ser Leu Ala Ile Leu Thr Leu Glu Met Thr Gly Asp Gln
               1445                1450                1455

Arg Glu Val Gly Ser Leu Gly Thr Ser Ala Thr Asn Ser Val Thr Tyr
           1460                1465                1470

Lys Lys Val Glu Asn Thr Val Leu Pro Lys Pro Asp Leu Pro Lys Thr
       1475                1480                1485

Ser Gly Lys Val Glu Leu Leu Pro Lys Val His Ile Tyr Gln Lys Asp
   1490                1495                1500

Leu Phe Pro Thr Glu Thr Ser Asn Gly Ser Pro Gly His Leu Asp Leu
1505                1510                1515                1520

Val Glu Gly Ser Leu Leu Gln Gly Thr Glu Gly Ala Ile Lys Trp Asn
               1525                1530                1535

Glu Ala Asn Arg Pro Gly Lys Val Pro Phe Leu Arg Val Ala Thr Glu
           1540                1545                1550

Ser Ser Ala Lys Thr Pro Ser Lys Leu Leu Asp Pro Leu Ala Trp Asp
       1555                1560                1565

Asn His Tyr Gly Thr Gln Ile Pro Lys Glu Glu Trp Lys Ser Gln Glu
   1570                1575                1580

Lys Ser Pro Glu Lys Thr Ala Phe Lys Lys Lys Asp Thr Ile Leu Ser
1585                1590                1595                1600

Leu Asn Ala Cys Glu Ser Asn His Ala Ile Ala Ala Ile Asn Glu Gly
               1605                1610                1615

Gln Asn Lys Pro Glu Ile Glu Val Thr Trp Ala Lys Gln Gly Arg Thr
           1620                1625                1630

Glu Arg Leu Cys Ser Gln Asn Pro Pro Val Leu Lys Arg His Gln Arg
       1635                1640                1645

Glu Ile Thr Arg Thr Thr Leu Gln Ser Asp Gln Glu Glu Ile Asp Tyr
   1650                1655                1660

Asp Asp Thr Ile Ser Val Glu Met Lys Lys Glu Asp Phe Asp Ile Tyr
1665                1670                1675                1680

Asp Glu Asp Glu Asn Gln Ser Pro Arg Ser Phe Gln Lys Lys Thr Arg
```

-continued

```
            1685                1690                1695

His Tyr Phe Ile Ala Ala Val Glu Arg Leu Trp Asp Tyr Gly Met Ser
        1700                1705                1710

Ser Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe Thr
  1730                1735                1740

Gln Pro Leu Tyr Arg Gly Glu Leu Asn Glu His Leu Gly Leu Leu Gly
1745                1750                1755                1760

Pro Tyr Ile Arg Ala Glu Val Glu Asp Asn Ile Met Val Thr Phe Arg
            1765                1770                1775

Asn Gln Ala Ser Arg Pro Tyr Ser Phe Tyr Ser Ser Leu Ile Ser Tyr
        1780                1785                1790

Glu Glu Asp Gln Arg Gln Gly Ala Glu Pro Arg Lys Asn Phe Val Lys
    1795                1800                1805

Pro Asn Glu Thr Lys Thr Tyr Phe Trp Lys Val Gln His His Met Ala
  1810                1815                1820

Pro Thr Lys Asp Glu Phe Asp Cys Lys Ala Trp Ala Tyr Phe Ser Asp
1825                1830                1835                1840

Val Asp Leu Glu Lys Asp Val His Ser Gly Leu Ile Gly Pro Leu Leu
            1845                1850                1855

Val Cys His Thr Asn Thr Leu Asn Pro Ala His Gly Arg Gln Val Thr
        1860                1865                1870

Val Gln Glu Phe Ala Leu Phe Phe Thr Ile Phe Asp Glu Thr Lys Ser
    1875                1880                1885

Trp Tyr Phe Thr Glu Asn Met Glu Arg Asn Cys Arg Ala Pro Cys Asn
  1890                1895                1900

Ile Gln Met Glu Asp Pro Thr Phe Lys Glu Asn Tyr Arg Phe His Ala
1905                1910                1915                1920

Ile Asn Gly Tyr Ile Met Asp Thr Leu Pro Gly Leu Val Met Ala Gln
            1925                1930                1935

Asp Gln Arg Ile Arg Trp Tyr Leu Leu Ser Met Gly Ser Asn Glu Asn
        1940                1945                1950

Ile His Ser Ile His Phe Ser Gly His Val Phe Thr Val Arg Lys Lys
    1955                1960                1965

Glu Glu Tyr Lys Met Ala Leu Tyr Asn Leu Tyr Pro Gly Val Phe Glu
  1970                1975                1980

Thr Val Glu Met Leu Pro Ser Lys Ala Gly Ile Trp Arg Val Glu Cys
1985                1990                1995                2000

Leu Ile Gly Glu His Leu His Ala Gly Met Ser Thr Leu Phe Leu Val
            2005                2010                2015

Tyr Ser Asn Lys Cys Gln Thr Pro Leu Gly Met Ala Ser Gly His Ile
        2020                2025                2030

Arg Asp Phe Gln Ile Thr Ala Ser Gly Gln Tyr Gly Gln Trp Ala Pro
    2035                2040                2045

Lys Leu Ala Arg Leu His Tyr Ser Gly Ser Ile Asn Ala Trp Ser Thr
  2050                2055                2060

Lys Glu Pro Phe Ser Trp Ile Lys Val Asp Leu Leu Ala Pro Met Ile
2065                2070                2075                2080

Ile His Gly Ile Lys Thr Gln Gly Ala Arg Gln Lys Phe Ser Ser Leu
            2085                2090                2095

Tyr Ile Ser Gln Phe Ile Ile Met Tyr Ser Leu Asp Gly Lys Lys Trp
        2100                2105                2110
```

```
Gln Thr Tyr Arg Gly Asn Ser Thr Gly Thr Leu Met Val Phe Phe Gly
       2115                2120                2125

Asn Val Asp Ser Ser Gly Ile Lys His Asn Ile Phe Asn Pro Pro Ile
   2130                2135                2140

Ile Ala Arg Tyr Ile Arg Leu His Pro Thr His Tyr Ser Ile Arg Ser
2145                2150                2155                2160

Thr Leu Arg Met Glu Leu Met Gly Cys Asp Leu Asn Ser Cys Ser Met
               2165                2170                2175

Pro Leu Gly Met Glu Ser Lys Ala Ile Ser Asp Ala Gln Ile Thr Ala
           2180                2185                2190

Ser Ser Tyr Phe Thr Asn Met Phe Ala Thr Trp Ser Pro Ser Lys Ala
       2195                2200                2205

Arg Leu His Leu Gln Gly Arg Ser Asn Ala Trp Arg Pro Gln Val Asn
   2210                2215                2220

Asn Pro Lys Glu Trp Leu Gln Val Asp Phe Gln Lys Thr Met Lys Val
2225                2230                2235                2240

Thr Gly Val Thr Thr Gln Gly Val Lys Ser Leu Leu Thr Ser Met Tyr
               2245                2250                2255

Val Lys Glu Phe Leu Ile Ser Ser Ser Gln Asp Gly His Gln Trp Thr
           2260                2265                2270

Leu Phe Phe Gln Asn Gly Lys Val Lys Val Phe Gln Gly Asn Gln Asp
       2275                2280                2285

Ser Phe Thr Pro Val Val Asn Ser Leu Asp Pro Pro Leu Leu Thr Arg
   2290                2295                2300

Tyr Leu Arg Ile His Pro Gln Ser Trp Val His Gln Ile Ala Leu Arg
2305                2310                2315                2320

Met Glu Val Leu Gly Cys Glu Ala Gln Asp Leu Tyr
               2325                2330
```

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Oligonucleotide primer

<400> SEQUENCE: 3
gtggattcat ctgggataaa acac 24

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Oligonucleotide primer

<400> SEQUENCE: 4
aggagaccag gtggcaaaga tattggtaaa gtaggatga 39

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Oligonucleotide primer

<400> SEQUENCE: 5
tgaaggagac caggtggcca acatattggt aaagtagga 39

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Oligonucleotide primer

<400> SEQUENCE: 6
ccactctttt ggattattgg cctgaggtct ccaggcatt 39

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: Oligonucleotide primer

<400> SEQUENCE: 7
gtccacttgc agccactcct ctggattatt cacctgagg 39

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Oligonucleotide primer

<400> SEQUENCE: 8
cttcacatac atgctggtga acagagattt tactccctg 39

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Oligonucleotide primer

<400> SEQUENCE: 9
aggagaccag gtggccaaga tattggtaaa gtaggatga 39

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Oligonucleotide primer

<400> SEQUENCE: 10
cacttgcagc cactcctctg gattattggc ctgaggtctc caggc 45

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Oligonucleotide primer

<400> SEQUENCE: 11

-continued agtttttcta caacagagga a 21

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: Oligonucleotide primer

<400> SEQUENCE: 12
tcatcctact ttaccaatat ctttgccacc tggtctcct 39

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Oligonucleotide primer

<400> SEQUENCE: 13
tcctacttta ccaatatgtt ggccacctgg tctccttca 39

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: Oligonucleotide primer

<400> SEQUENCE: 14
aatgcctgga gacctcaggc caataatcca aaagagtgg 39

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Oligonucleotide primer

<400> SEQUENCE: 15
cctcaggtga ataatccaga ggagtggctg caagtggac 39

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Oligonucleotide primer

<400> SEQUENCE: 16
cagggagtaa aatctctgtt caccagcatg tatgtgaag 39

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 17
tcatcctact ttaccaatat cttggccacc tggtctcct 39

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Oligonucleotide primer

<400> SEQUENCE: 18
gcctggagac ctcaggccaa taatccagag gagtggctgc aagtg 45

<210> SEQ ID NO 19
<211> LENGTH: 160
<212> TYPE: PRT
<213> ORGANISM: Porcine

<400> SEQUENCE: 19

```
Ser Cys Ser Met Pro Leu Gly Met Gln Asn Lys Ala Ile Ser Asp Ser
  1               5                  10                  15

Gln Ile Thr Ala Ser Ser His Leu Ser Asn Ile Phe Ala Thr Trp Ser
             20                  25                  30

Pro Ser Gln Ala Arg Leu His Leu Gln Gly Arg Thr Asn Ala Trp Arg
         35                  40                  45

Pro Arg Val Ser Ser Ala Glu Glu Trp Leu Gln Val Asp Leu Gln Lys
     50                  55                  60

Thr Val Lys Val Thr Gly Ile Thr Thr Gln Gly Val Lys Ser Leu Leu
 65                  70                  75                  80

Ser Ser Met Tyr Val Lys Glu Phe Leu Val Ser Ser Ser Gln Asp Gly
                 85                  90                  95

Arg Arg Trp Thr Leu Phe Leu Gln Asp Gly His Thr Lys Val Phe Gln
            100                 105                 110

Gly Asn Gln Asp Ser Ser Thr Pro Val Val Asn Ala Leu Asp Pro Pro
        115                 120                 125

Leu Phe Thr Arg Tyr Leu Arg Ile His Pro Thr Ser Trp Ala Gln His
    130                 135                 140

Ile Ala Leu Arg Leu Glu Val Leu Gly Cys Glu Ala Gln Asp Leu Tyr
145                 150                 155                 160
```

<210> SEQ ID NO 20
<211> LENGTH: 160
<212> TYPE: PRT
<213> ORGANISM: murine

<400> SEQUENCE: 20

```
Ser Cys Ser Ile Pro Leu Gly Met Glu Ser Lys Val Ile Ser Asp Thr
  1               5                  10                  15

Gln Ile Thr Ala Ser Ser Tyr Phe Thr Asn Met Phe Ala Thr Trp Ser
             20                  25                  30

Pro Ser Gln Ala Arg Leu His Leu Gln Gly Arg Thr Asn Ala Trp Arg
         35                  40                  45

Pro Gln Val Asn Asp Pro Lys Gln Trp Leu Gln Val Asp Leu Gln Lys
     50                  55                  60

Thr Met Lys Val Thr Gly Ile Ile Thr Gln Gly Val Lys Ser Leu Phe
 65                  70                  75                  80

Thr Ser Met Phe Val Lys Glu Phe Leu Ile Ser Ser Ser Gln Asp Gly
                 85                  90                  95

His His Trp Thr Gln Ile Leu Tyr Asn Gly Lys Val Lys Val Phe Gln
```

-continued

```
            100                 105                 110

Gly Asn Gln Asp Ser Ser Thr Pro Met Met Asn Ser Leu Asp Pro Pro
        115                 120                 125

Leu Leu Thr Arg Tyr Leu Arg Ile His Pro Gln Ile Trp Glu His Gln
    130                 135                 140

Ile Ala Leu Arg Leu Glu Ile Leu Gly Cys Glu Ala Gln Gln Gln Tyr
145                 150                 155                 160


<210> SEQ ID NO 21
<211> LENGTH: 160
<212> TYPE: PRT
<213> ORGANISM: canine

<400> SEQUENCE: 21

Ser Cys Ser Met Pro Leu Gly Met Glu Ser Lys Ala Ile Ser Asp Ala
  1               5                  10                  15

Gln Ile Thr Ala Ser Ser Tyr Leu Ser Ser Met Leu Ala Thr Trp Ser
            20                  25                  30

Pro Ser Gln Ala Arg Leu His Leu Gln Gly Arg Thr Asn Ala Trp Arg
        35                  40                  45

Pro Gln Ala Asn Asn Pro Lys Glu Trp Leu Gln Val Asp Phe Arg Lys
    50                  55                  60

Thr Met Lys Val Thr Gly Ile Thr Thr Gln Gly Val Lys Ser Leu Leu
 65                  70                  75                  80

Ile Ser Met Tyr Val Lys Glu Phe Leu Ile Ser Ser Ser Gln Asp Gly
                85                  90                  95

His Asn Gln Thr Leu Phe Leu Gln Asn Gly Lys Val Lys Val Phe Gln
            100                 105                 110

Gly Asn Arg Asp Ser Ser Thr Pro Val Arg Asn Arg Leu Glu Pro Pro
        115                 120                 125

Leu Val Ala Arg Tyr Val Arg Leu His Pro Gln Ser Trp Ala His His
    130                 135                 140

Ile Ala Leu Arg Leu Glu Val Leu Gly Cys Asp Thr Gln Gln Pro Ala
145                 150                 155                 160
```